US012640028B2

(12) United States Patent
Mcgahren et al.

(10) Patent No.: US 12,640,028 B2
(45) Date of Patent: May 26, 2026

(54) SHUTTING OFF AN ALARM IN A MEDICAMENT DELIVERY DEVICE WITHOUT HARMING AN INTERNAL PRINTED CIRCUIT BOARD ASSEMBLY

(71) Applicant: INSULET CORPORATION, Acton, MA (US)

(72) Inventors: Lucas Mcgahren, Somerville, MA (US); Ayden Henson, Arlington, MA (US); Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 138 days.

(21) Appl. No.: 18/530,453

(22) Filed: Dec. 6, 2023

(65) Prior Publication Data

US 2024/0203231 A1 Jun. 20, 2024

Related U.S. Application Data

(60) Provisional application No. 63/476,221, filed on Dec. 20, 2022.

(51) Int. Cl.
| | |
|---|---|
| *G08B 25/00* | (2006.01) |
| *A61M 5/142* | (2006.01) |
| *G08B 7/06* | (2006.01) |

(52) U.S. Cl.
CPC ....... *G08B 25/008* (2013.01); *A61M 5/14248* (2013.01); *G08B 7/06* (2013.01); *A61M 2205/18* (2013.01)

(58) Field of Classification Search
CPC ...... A61M 2205/581; A61M 2205/332; A61M 2205/505; A61M 2205/583;
(Continued)

(56) References Cited

U.S. PATENT DOCUMENTS

| | | | |
|---|---|---|---|
| 441,663 | A | 12/1890 | Hofbauer |
| 955,911 | A | 4/1910 | Saegmuller |

(Continued)

FOREIGN PATENT DOCUMENTS

| | | |
|---|---|---|
| CA | 2863379 A1 | 8/2013 |
| CN | 201134101 Y | 10/2008 |

(Continued)

OTHER PUBLICATIONS

European Search Report for the European Patent Application No. EP03743667, dated Jul. 22, 2008.

(Continued)

*Primary Examiner* — Daniel Previl
(74) *Attorney, Agent, or Firm* — Goodwin Procter LLP

(57) ABSTRACT

The exemplary embodiments may provide and approach to shutting off the alarm of a medicament delivery device without harming the internal printed circuit board assembly (PCBA) of the medicament delivery device. As a result, the PCBA of the medicament delivery device may not be damaged and can be harvested for reuse. Some exemplary embodiments may provide a displaceable component that may be displaced to open an electrical circuit that powers an alarm of the medicament delivery device. In other exemplary embodiments, a user may break the electrically conductive element, such as by applying sufficient force with a tool. In still other exemplary embodiments, the alarm may be shut off by mechanical manipulation of the medicament delivery device.

16 Claims, 27 Drawing Sheets

(58) Field of Classification Search
CPC ........ A61M 2005/2073; A61M 5/2053; A61M
5/24; A61M 15/009; A61M 5/19; A61M
2205/50; A61M 2205/582; A61M
2205/8206; A61M 2005/206; A61M
2205/18; A61M 2205/587; A61M 5/3202;
A61M 2005/208; A61M 2005/2086;
A61M 2005/2481; A61M 2005/31588;
A61M 2202/07; A61M 2205/14; A61M
2205/3306; A61M 2205/3313; A61M
2205/3592; A61M 2205/584; A61M
2205/6009; A61M 2209/086; A61M
5/2033; A61M 5/2448; A61M 5/2455;
A61M 5/31568; A61M 5/46; A61M
15/0001; A61M 2005/3125; A61M
2205/6027; A61M 2205/6063; A61M
5/31; A61M 5/3287; A61M 5/5086;
A61M 15/0021; A61M 15/0086; A61M
16/0003; A61M 16/0006; A61M 16/0051;
A61M 16/024; A61M 2016/0027; A61M
2016/0039; A61M 2205/13; A61M
2205/3327; A61M 2205/3331; A61M
2205/3561; A61M 2205/3569; A61M
2205/43; A61M 2205/44; A61M 5/14244;
A61M 5/14248; A61M 2205/3334; A61M
2205/70; A61M 2005/14252; A61M
2005/14268; A61M 2005/16863; A61M
5/1413; A61M 5/16886; A61M
2005/14264; A61M 2205/0244; A61M
2205/3344; A61M 2205/3358; A61M
5/16854; A61M 5/20; A61M 2205/52;
A61M 2205/3368; A61M 2205/3584;
A61M 2205/6054; A61M 2207/00; A61M
5/16831; A61M 2205/3553; A61M 5/14;
A61M 5/145; A61M 5/16859; A61M
2005/14256; A61M 2205/7527; A61M
2205/8237; A61M 5/3158; A61M
2005/1726; A61M 2205/3375; A61M
11/06; A61M 15/0016; A61M 15/002;
A61M 15/0036; A61M 15/004; A61M
15/008; A61M 15/08; A61M 16/14;
A61M 16/208; A61M 2005/2013; A61M
2016/0024; A61M 2016/0033; A61M
2202/064; A61M 5/152; A61M 5/1723;
A61M 2205/0294; A61M 2205/3303;
A61M 2205/3341; A61M 2205/502;
A61M 2205/8212; A61M 2206/22; A61M
5/422; A61M 11/002; A61M 11/005;
A61M 11/007; A61M 11/041; A61M
11/042; A61M 11/047; A61M 15/0008;
A61M 15/0015; A61M 15/0018; A61M
15/0028; A61M 15/0045; A61M 15/0066;
A61M 15/0085; A61M 15/0091; A61M
15/0093; A61M 15/0095; A61M 15/02;
A61M 15/025; A61M 15/06; A61M
16/0063; A61M 16/0066; A61M 16/0093;
A61M 16/0866; A61M 16/101; A61M
16/105; A61M 16/1055; A61M 16/1065;
A61M 16/204; A61M 16/209; A61M
2005/1657; A61M 2202/0208; A61M
2202/0225; A61M 2202/0241; A61M
2202/025; A61M 2202/0266; A61M
2202/0275; A61M 2202/0283; A61M
2202/30; A61M 2205/07; A61M
2205/3653; A61M 2205/6018; A61M
2205/6072; A61M 2205/7509; A61M
2205/7518; A61M 2205/7536; A61M
2205/7545; A61M 2205/8262; A61M
2205/8268; A61M 2209/088; A61M
2210/0618; A61M 2210/065; A61M
2210/1028; A61M 2210/1032; A61M
2210/1035; A61M 2210/1039; A61M
5/1409; A61M 5/165; A61M 5/425;
A61M 16/022; A61M 16/0833; A61M
16/161; A61M 2005/1402; A61M
2005/14208; A61M 2005/14288; A61M
2005/14506; A61M 2005/1581; A61M
2005/1583; A61M 2005/1585; A61M
2005/1586; A61M 2016/0036; A61M
2202/0007; A61M 2205/0266; A61M
2205/04; A61M 2205/16; A61M
2205/3317; A61M 2205/3337; A61M
2205/3379; A61M 2205/3389; A61M
2205/3523; A61M 2205/3546; A61M
2205/3576; A61M 2205/3606; A61M
2205/80; A61M 2209/00; A61M
2209/045; A61M 2209/10; A61M
2230/201; A61M 2230/40; A61M
2230/42; A61M 5/141; A61M 5/142;
A61M 5/14212; A61M 5/14216; A61M
5/14224; A61M 5/14232; A61M 5/1452;
A61M 5/14586; A61M 5/148; A61M
5/158; A61M 5/162; A61M 5/168; A61M
5/16804; A61M 5/16809; A61M 5/16813;
A61M 5/172; A61M 5/31533; A61M
5/3157; A61M 5/365; A61M 2005/16868;
A61M 5/16836; A61M 1/00; A61M 3/00;
A61M 5/00; A61M 9/00; A61M 11/00;
A61M 13/00; A61M 15/00; A61M 16/00;
A61M 19/00; G09B 23/285; G09B 23/28;
G06Q 10/00; G06Q 30/018; G06Q 50/06;
A61N 1/0502; A61N 1/306; A61N 1/325;
A61N 1/327; A61N 1/0412; A61N
1/0436; A61N 1/044; A61N 1/0448;
A61K 31/711; A61K 2039/53; A61K
2039/54; A61K 39/292; A61K 31/445;
A61K 47/32; A61K 9/0014; A61K
9/5026; A61B 17/205; A61B 2560/0462;
A61B 2562/0247; A61B 5/0002; A61B
5/0876; A61B 5/091; A61B 5/097; A61B
5/14532; A61B 5/14546; A61B 5/15003;
A61B 5/150229; A61B 5/150389; A61B
5/150503; A61B 5/150809; A61B
5/150816; A61B 5/150824; A61B
5/15087; A61B 5/153; A61B 5/155; A61B
5/157; A61B 5/412; A61B 5/4833; A61B
5/4839; A61B 5/682; A61B 5/7275; A61B
5/7282; A61B 5/742; A61B 5/6833; A61B
5/01; A61B 5/02055; A61B 2562/0204;
A61B 2562/029; A61B 2562/08; A61B
5/02042; A61B 5/02438; A61B 5/444;
A61B 5/1118; A61B 2560/0242; A61B
5/002; A61B 5/021; A61B 5/024; A61B
5/03; A61B 5/053; A61B 5/7405; A61B
5/7455; A61B 2562/0233; A61B
2562/0271; A61B 5/688; A61B
2560/0412; A61B 5/0024; A61B 5/087;
A61B 5/1427; A61B 5/150022; A61B
5/150175; A61B 5/150358; A61B
5/15107; A61B 5/15117; A61B 5/15119;

A61B 5/15121; A61B 5/15123; A61B
5/15125; A61B 5/15186; A61B 5/4848;
A61B 5/74; A61B 5/0022; A61B 5/02;
A61B 5/0205; A61B 5/14865; A61B
5/4866; A61B 5/7246; A61B 5/7267;
A61B 1/00; A61P 31/20; C12N 15/8206;
C12N 15/86; C12N 2730/10111; C12N
2730/10134; C12N 2730/10171; C12N
7/00; G16H 20/17; G16H 20/30; G16H
40/67; G16H 15/00; G16H 20/40; G08B
25/008; G08B 7/06; A24F 40/10; A24F
40/485; A24F 15/015; A24F 40/42; A24F
40/50; A24F 40/60; A24F 40/90; G01N
2027/222; G01N 27/02; G01N 27/026;
G01N 27/221; G01N 27/4145; G01N
27/447; G01N 27/72; G01N 22/00; G01N
33/0031; G02F 1/167; H04L 63/1416;
H04L 9/3247; H04L 67/12; Y02A 90/10;
H05B 1/0244; H05B 2203/016; H05B
3/265; A61J 1/20; A63B 2220/13; A63B
2220/17; A63B 2220/40; A63B 2220/56;
A63B 2220/72; A63B 2220/75; A63B
2220/805; A63B 23/18; A63B 2024/0078;
A63B 24/0075; B23P 15/00; F04B 43/02;
F04B 43/09; F04B 43/1253; F04B 7/00;
F04C 2230/60; G01F 1/28; G01F 22/00;
G05B 23/02; G05D 7/0647; G05D
7/0676; G08C 17/02; H04B 7/2609;
H04W 4/026; H04W 4/027; H04W 4/029;
H04W 4/35; H04W 4/80; H04W 4/38;
Y02E 60/10; Y10T 29/49236; Y10T
29/494; Y10T 29/49412; Y10T 29/49826;
Y10T 29/49828; H01Q 13/20; H01Q
13/203
USPC ............... 340/501, 506, 517, 521, 525, 530,
340/538.12, 539.13, 539.22, 545.7, 568.8,
340/635, 636.1, 641, 653
See application file for complete search history.

(56) References Cited

U.S. PATENT DOCUMENTS

| | | | |
|---|---|---|---|
| 4,206,401 A | 6/1980 | Meyer | |
| 4,277,226 A | 7/1981 | Archibald | |
| 4,307,713 A | 12/1981 | Galkin et al. | |
| 4,398,542 A | 8/1983 | Cunningham et al. | |
| 4,560,979 A | 12/1985 | Rosskopf | |
| 4,587,850 A | 5/1986 | Moser | |
| 4,689,603 A * | 8/1987 | Conigliaro | B60K 28/063 |
| | | | 340/576 |
| 4,801,957 A | 1/1989 | Vandemoere | |
| 4,836,752 A | 6/1989 | Burkett | |
| 4,850,954 A | 7/1989 | Charvin | |
| 4,882,600 A | 11/1989 | Van de Moere | |
| 4,961,055 A | 10/1990 | Habib et al. | |
| 4,973,998 A | 11/1990 | Gates | |
| 5,045,871 A | 9/1991 | Reinholdson | |
| 5,239,326 A | 8/1993 | Takai | |
| 5,452,033 A | 9/1995 | Balling et al. | |
| 5,563,584 A | 10/1996 | Rader et al. | |
| 5,576,781 A | 11/1996 | Deleeuw | |
| 5,585,733 A | 12/1996 | Paglione | |
| 5,586,553 A | 12/1996 | Halili et al. | |
| 5,647,853 A | 7/1997 | Feldmann et al. | |
| 5,660,163 A | 8/1997 | Schulman et al. | |
| 5,726,404 A | 3/1998 | Brody | |
| 5,726,751 A | 3/1998 | Altendorf et al. | |
| 5,785,681 A | 7/1998 | Indravudh et al. | |
| 5,800,420 A | 9/1998 | Gross et al. | |
| 5,830,999 A | 11/1998 | Dunn | |

| | | | |
|---|---|---|---|
| 5,867,688 A | 2/1999 | Simmon et al. | |
| 5,899,882 A | 5/1999 | Waksman et al. | |
| 6,171,264 B1 | 1/2001 | Bader | |
| 6,381,029 B1 | 4/2002 | Tipirneni | |
| 6,685,452 B2 | 2/2004 | Christiansen et al. | |
| 6,768,319 B2 | 7/2004 | Wang | |
| 6,830,558 B2 | 12/2004 | Flaherty et al. | |
| 7,018,360 B2 | 3/2006 | Flaherty et al. | |
| 7,128,727 B2 | 10/2006 | Flaherty et al. | |
| 7,144,384 B2 | 12/2006 | Gorman et al. | |
| 7,182,726 B2 | 2/2007 | Williams et al. | |
| 7,303,073 B2 | 12/2007 | Raynal-Olive et al. | |
| 8,056,719 B2 | 11/2011 | Porret et al. | |
| 8,105,282 B2 | 1/2012 | Susi et al. | |
| 8,285,487 B2 | 10/2012 | Bergstrom et al. | |
| 8,454,557 B1 | 6/2013 | Qi et al. | |
| 8,461,561 B2 | 6/2013 | Freeman et al. | |
| 8,727,117 B2 | 5/2014 | Maasarani | |
| 9,005,166 B2 | 4/2015 | Uber, III et al. | |
| 9,248,229 B2 | 2/2016 | Devouassoux et al. | |
| 9,427,710 B2 | 8/2016 | Jansen | |
| 9,598,195 B2 | 3/2017 | Deutschle et al. | |
| 9,862,519 B2 | 1/2018 | Deutschle et al. | |
| 10,046,114 B1 | 8/2018 | Biederman et al. | |
| 10,086,131 B2 | 10/2018 | Okihara | |
| 10,342,926 B2 | 7/2019 | Nazzaro et al. | |
| 10,441,717 B2 | 10/2019 | Schmid et al. | |
| 2002/0032374 A1 | 3/2002 | Holker et al. | |
| 2002/0161307 A1 | 10/2002 | Yu et al. | |
| 2003/0073952 A1 | 4/2003 | Flaherty et al. | |
| 2004/0010207 A1 | 1/2004 | Flaherty et al. | |
| 2004/0010507 A1 | 1/2004 | Bellew | |
| 2004/0085215 A1 | 5/2004 | Moberg et al. | |
| 2004/0215492 A1 | 10/2004 | Choi | |
| 2005/0055242 A1 | 3/2005 | Bello et al. | |
| 2005/0238507 A1 | 10/2005 | Dilanni et al. | |
| 2006/0051404 A1 * | 3/2006 | Yeshurun | A61B 17/205 |
| | | | 424/449 |
| 2006/0086909 A1 | 4/2006 | Schaber | |
| 2006/0092569 A1 | 5/2006 | Che et al. | |
| 2006/0264926 A1 | 11/2006 | Kochamba | |
| 2006/0282290 A1 | 12/2006 | Flaherty et al. | |
| 2007/0027370 A1 | 2/2007 | Brauker et al. | |
| 2007/0078784 A1 | 4/2007 | Donovan et al. | |
| 2007/0118405 A1 | 5/2007 | Campbell et al. | |
| 2007/0179885 A1 | 8/2007 | Bird et al. | |
| 2007/0191770 A1 | 8/2007 | Moberg et al. | |
| 2007/0233051 A1 | 10/2007 | Hohl et al. | |
| 2008/0004515 A1 | 1/2008 | Jennewine | |
| 2008/0027371 A1 | 1/2008 | Higuchi et al. | |
| 2008/0033272 A1 | 2/2008 | Gough et al. | |
| 2008/0059133 A1 * | 3/2008 | Edwards | A61M 15/009 |
| | | | 703/7 |
| 2008/0077081 A1 | 3/2008 | Mounce et al. | |
| 2008/0173073 A1 | 7/2008 | Downie et al. | |
| 2008/0234628 A1 * | 9/2008 | Dent | A61N 1/303 |
| | | | 604/20 |
| 2008/0255438 A1 | 10/2008 | Saidara et al. | |
| 2008/0269723 A1 | 10/2008 | Mastrototaro et al. | |
| 2008/0281290 A1 | 11/2008 | Yodfat et al. | |
| 2009/0048556 A1 | 2/2009 | Durand | |
| 2009/0062767 A1 | 3/2009 | Van Antwerp et al. | |
| 2009/0069787 A1 | 3/2009 | Estes et al. | |
| 2009/0112769 A1 | 4/2009 | Dicks et al. | |
| 2009/0177142 A1 | 7/2009 | Blomquist et al. | |
| 2009/0254041 A1 | 10/2009 | Krag et al. | |
| 2010/0076275 A1 | 3/2010 | Chu et al. | |
| 2010/0094251 A1 | 4/2010 | Estes | |
| 2010/0114026 A1 | 5/2010 | Karratt et al. | |
| 2010/0137784 A1 | 6/2010 | Cefai et al. | |
| 2010/0145272 A1 | 6/2010 | Cefai et al. | |
| 2010/0185175 A1 | 7/2010 | Kamen et al. | |
| 2010/0286997 A1 | 11/2010 | Srinivasan | |
| 2011/0124996 A1 | 5/2011 | Reinke et al. | |
| 2011/0142688 A1 | 6/2011 | Chappel et al. | |
| 2011/0152658 A1 | 6/2011 | Peyser et al. | |
| 2011/0213306 A1 | 9/2011 | Hanson et al. | |
| 2011/0218495 A1 | 9/2011 | Remebe | |
| 2011/0225024 A1 | 9/2011 | Seyer et al. | |

(56) References Cited

U.S. PATENT DOCUMENTS

| | | |
|---|---|---|
| 2011/0246235 A1 | 10/2011 | Powell et al. |
| 2011/0313680 A1 | 12/2011 | Doyle, III |
| 2011/0316562 A1 | 12/2011 | Cefai et al. |
| 2012/0029941 A1 | 2/2012 | Malave et al. |
| 2012/0050046 A1 | 3/2012 | Satorius et al. |
| 2012/0054841 A1 | 3/2012 | Schultz et al. |
| 2012/0092837 A1* | 4/2012 | Tanaka ................ H05K 1/0281 |
| | | 174/254 |
| 2012/0153936 A1 | 6/2012 | Romani et al. |
| 2012/0182939 A1 | 7/2012 | Rajan et al. |
| 2012/0184909 A1 | 7/2012 | Gyrn |
| 2012/0203085 A1 | 8/2012 | Rebec |
| 2012/0232520 A1 | 9/2012 | Sloan et al. |
| 2012/0245515 A1* | 9/2012 | Calasso ............... A61M 5/1413 |
| | | 604/67 |
| 2012/0265166 A1 | 10/2012 | Yodfat |
| 2012/0277667 A1 | 11/2012 | Yodat et al. |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0080832 A1 | 3/2013 | Dean et al. |
| 2013/0138452 A1 | 5/2013 | Cork et al. |
| 2013/0173473 A1 | 7/2013 | Birtwhistle et al. |
| 2013/0245545 A1 | 9/2013 | Arnold et al. |
| 2013/0274576 A1 | 10/2013 | Amirouche et al. |
| 2014/0114277 A1 | 4/2014 | Eggert et al. |
| 2014/0163664 A1* | 6/2014 | Goldsmith ......... A61B 17/0057 |
| | | 604/93.01 |
| 2014/0180203 A1 | 6/2014 | Budiman et al. |
| 2014/0188398 A1* | 7/2014 | Cohen .................. A61B 5/0004 |
| | | 702/19 |
| 2015/0038898 A1 | 2/2015 | Palmer et al. |
| 2015/0057913 A1 | 2/2015 | Benhammou |
| 2015/0119666 A1 | 4/2015 | Brister et al. |
| 2015/0290391 A1 | 10/2015 | Schmid et al. |
| 2016/0022905 A1 | 1/2016 | Nagar et al. |
| 2016/0184517 A1 | 6/2016 | Baek et al. |
| 2016/0339172 A1 | 11/2016 | Michaud et al. |
| 2017/0173261 A1 | 6/2017 | O'Connor et al. |
| 2018/0040255 A1 | 2/2018 | Freeman et al. |
| 2018/0204636 A1* | 7/2018 | Edwards ................ G16H 40/67 |
| 2018/0280609 A1 | 10/2018 | Nishimura et al. |
| 2018/0296757 A1 | 10/2018 | Finan et al. |
| 2022/0203023 A1* | 6/2022 | O'Connor ............. A61M 5/168 |
| 2022/0218920 A1* | 7/2022 | Roche .................... H05K 3/308 |

FOREIGN PATENT DOCUMENTS

| | | |
|---|---|---|
| EP | 1762263 A1 | 3/2007 |
| EP | 1839694 A1 | 10/2007 |
| EP | 1852703 A1 | 11/2007 |
| EP | 2099384 A1 | 9/2009 |
| EP | 2353628 A2 | 8/2011 |
| EP | 1874390 B1 | 10/2014 |
| EP | 3068290 A1 | 9/2016 |
| EP | 3187201 A1 | 7/2017 |
| EP | 3598942 A1 | 1/2020 |
| EP | 3607985 A1 | 2/2020 |
| ES | 2559866 T3 | 2/2016 |
| GB | 1401588 A | 7/1975 |
| GB | 2176595 A | 12/1986 |
| GB | 2443260 A | 4/2008 |
| GB | 2443261 A | 4/2008 |
| GB | 2461086 A | 12/2009 |
| GB | 2495014 A | 3/2013 |
| GB | 2524717 A | 10/2015 |
| GB | 2525149 A | 10/2015 |
| JP | 2001190659 A | 7/2001 |
| JP | 2003154190 A | 5/2003 |
| JP | 2007144141 A1 | 6/2007 |
| JP | 2007307359 A | 11/2007 |
| JP | 2008242502 A | 10/2008 |
| JP | 2012210441 A | 11/2012 |
| WO | 9801071 A1 | 1/1998 |
| WO | 9819145 A1 | 5/1998 |
| WO | 9824495 A1 | 6/1998 |
| WO | 9841267 A1 | 9/1998 |
| WO | 0010628 A2 | 3/2000 |
| WO | 0013580 A1 | 3/2000 |
| WO | 0019887 A1 | 4/2000 |
| WO | 0061215 A1 | 10/2000 |
| WO | 0078210 A1 | 12/2000 |
| WO | 2005031631 A2 | 4/2005 |
| WO | 2006060668 A2 | 6/2006 |
| WO | 2007112034 A2 | 10/2007 |
| WO | 2008024814 A2 | 2/2008 |
| WO | 2009023634 A2 | 2/2009 |
| WO | 2009032399 A1 | 3/2009 |
| WO | 2010025433 A1 | 3/2010 |
| WO | 2010078434 A2 | 7/2010 |
| WO | 2010146579 A1 | 12/2010 |
| WO | 2011012465 A1 | 2/2011 |
| WO | 2011133823 A1 | 10/2011 |
| WO | 2013149186 A1 | 10/2013 |
| WO | 2014136105 A1 | 9/2014 |
| WO | 2015187793 A1 | 12/2015 |
| WO | 2016041873 A1 | 3/2016 |
| WO | 2016181384 A2 | 11/2016 |
| WO | 2017089289 A1 | 6/2017 |
| WO | 2017205816 A1 | 11/2017 |
| WO | 2019043702 A1 | 3/2019 |
| WO | 2019094440 A1 | 5/2019 |
| WO | 2020124058 A1 | 6/2020 |
| WO | 2022075662 A1 | 4/2022 |

OTHER PUBLICATIONS

International Search Report and Written Opinion mailed Sep. 9, 2016, issued in PCT Patent Application No. PCT/US2016/037189, 12 pages.

Preliminary Report on Patentability mailed Dec. 21, 2017, issued in PCT Patent Application No. PCT/US2016/037189.

U.K. Intellectual Property Office, GB Application No. GB 1401587. 9, "Search Report under Section 17(5)" Aug. 11, 2015, 1 page.

International Search Report and Written Opinion for PCT Application No. PCT/GB2015/050247, May 8, 2015, 14 pages.

Extended Search Report mailed Nov. 24, 2017, issued in European Patent Application No. 15779465.2, 10 pages.

International Search Report and Written Opinion for PCT Application No. PCT/US15/26875, mailed Jan. 18, 2016, 10 pages.

U.K. Intellectual Property Office, GB Application No. GB 1401588. 7, "Search Report under Section 17(5)" Aug. 17, 2015, 1 page.

U.K. Intellectual Property Office, GB Application No. GB 1401589. 5, "Search Report under Section 17" Jul. 27, 2015, 1 page.

International Search Report and Written Opinion for PCT Application No. PCT/GB2015/050250, May 7, 2015, 9 pages.

3GPP TS 23.003 V10.0.0.0 Numbering, addressing and identification. Dec. 2010.

International Search Report and Written Opinion for PCT Application No. PCT/GB2015/050251, Jun. 12, 2015, 9 pages.

European Search Report for the European Patent Application No. EP19194241, dated Oct. 22, 2019, 6 pages.

International Preliminary Report on Patentability for PCT/US2017/061095, issued on May 14, 2019, 6 pages.

International Search Report and Written Opinion for PCT/US18/52468, mailed on Feb. 26, 2019, 16 pages.

International Search Report and Written Opinion for PCT/US2017/061095, mailed on Feb. 20, 2018, 8 pages.

International Search Report and Written Opinion for the International Patent Application No. PCT/US2021/047690, mailed Jan. 14, 2022, 13 pages.

International Search Report and Written Opinion for the International Patent Application No. PCT/US2022/055745, mailed Feb. 14, 2022, 13 pages.

International Search Report and Written Opinion for the International Patent Application No. PCT/US2021/053162, mailed Mar. 28, 2022, 18 pages.

(56)  References Cited

OTHER PUBLICATIONS

International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.
International Search Report and Written Opinion for International Patent Application No. PCT/US2022/029012, mailed Aug. 19, 2022, 12 pages.

* cited by examiner

Figure 2A:
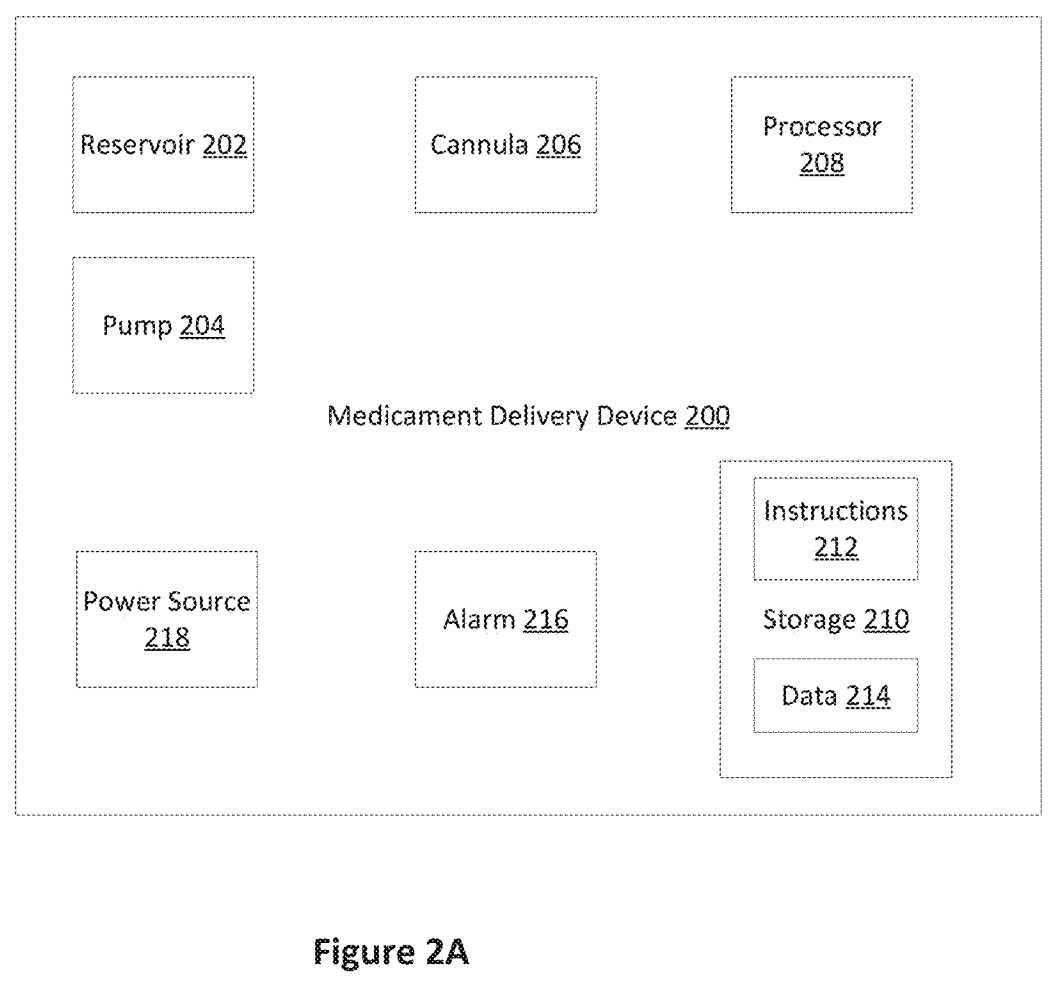

Medicament Delivery Device 200

Reservoir 202

Pump 204

Cannula 206

Processor 208

Power Source 218

Alarm 216

Storage 210

Instructions 212

Data 214

SHUTTING OFF AN ALARM IN A MEDICAMENT DELIVERY DEVICE WITHOUT HARMING AN INTERNAL PRINTED CIRCUIT BOARD ASSEMBLY

RELATED APPLICATIONS

This application claims the benefit of U.S. Provisional Patent Application No. 63/476,221, filed Dec. 20, 2022, the entire contents of which are incorporated herein by reference in its entirety.

BACKGROUND

Conventional medicament delivery devices may provide alarms that vibrate and/or generate audio output. The alarm is responsive to a detected condition or event about which the user needs to be informed. FIG. 1A depicts a flowchart of steps that may be taken with some conventional medicament delivery devices regarding alarms. At 102, the alarm is activated in response to a condition or event. At 104, the alarm is halted by breaking off a tab on an internal printed circuit board assembly (PCBA). FIG. 1B depicts an illustrative conventional PCBA 108 for a medicament delivery device. The alarm may be shut off by breaking tab 110 of the PCBA.

The difficulty with the breaking of the tab of the PCBA to shut off the alarm is that it results in damage to the PCBA. Although the medicament delivery devices may have a short lifespan, such as a few days, the PCBAs cannot be extracted and reused when the tab has been broken off.

SUMMARY

In accordance with an inventive facet, a medicament delivery device includes a printed circuit board containing electronic components and an alarm for creating an alarm sound and/or vibration. The medicament delivery device also includes an electrical circuit for carrying electricity to the alarm. At least a portion of the electrical circuit is in on the printed circuit board. The medicament delivery device further includes an electrically conductive element that is electrically connected to the electrical circuit, is separate from the printed circuit board, and is displaceable in response to a force to be no longer electrically connected to the electrical circuit without harming the printed circuit board. The medicament delivery device has a housing for housing the printed circuit board, alarm, and electrically conductive element, and a passage through the housing leading to the electrically conductive element. The passage is adapted for receiving a tool to apply the force to displace that electrically conductive element so that the electrically conductive element is no longer connected to the electrical circuit.

The electrically conductive element may be coupled to a plug that fits in a portion of the passage that is displaced by the force of the tool, which in turn displaces the electrically conductive element so as to be no longer electrically connected to electrical circuit. The plug may have deformable components that deform responsive to the force from the tool. The printed circuit board may include a plated through hole that is part of the passage and that is at least partially plated, and the electrically conductive element may be positioned in the plated through hole that is at least partially plated to be electrically connected to the electrical circuit. The electrically conductive element may be configured to be displaced out of the plated through hole that is at least partially plated by the force of the tool so as to no longer be electrically connected to the electrical circuit. The electrically conductive element may be a sheet metal clip that has a first portion positioned in the plated through hole that is at least partially plated and a second portion connected to another element in the electrical circuit. The electrically conductive element may be a clip that fits at least partially inside the plated through hole that is at least partially plated and is biased to contact plated walls of the plated through hole that is at least partially plated. The electrically conductive element may be a pin held between electrically conductive surfaces that is displaced to no longer be held between the electrically conductive surfaces by the force. The electrically conductive surfaces may be part of sheet metal clips. The medicament delivery device may include a chassis for the printed circuit board. The electrically conductive element may be a sheet metal clip connected at one end to the housing and connected at another end to at least one electrically conductive component on the printed circuit board. The chassis may press the clip down onto the electrically component. The sheet metal clip may be adapted to become dislodged from the chassis and to no longer be electrically connected to the electrical circuit when displaced by the force. There may be a plated through hole in the printed circuit board, and the electrically conductive element may be a sheet metal clip having a formed feature that plugs into the plated through holes to close the electrical circuit. The force from the tool may displace the formed feature from the plated through hole so that the electrically conductive element is no longer electrically connected to the electrical circuit.

In accordance with another inventive facet, a medicament delivery device includes a printed circuit board containing electronic components and an alarm for creating an alarm sound and/or vibration. The medicament delivery device also includes an electrical circuit for carrying electricity to the alarm generator. At least a portion of the electrical circuit is on the printed circuit board. The medicament delivery device further includes an electrically conductive element that is electrically connected to the electrical circuit, separate from the printed circuit board, and breakable in response to a force to break an electrical connection to the electrical circuit without harming the printed circuit board. The medicament delivery device additionally includes a housing for housing the printed circuit board, alarm, and electrically conductive element and a passage through the housing leading to the electrically conductive element. The passage is adapted for receiving a tool to apply the force to break the electrically conductive element so that the electrically conductive element is no longer connected to the electrical circuit.

The electrically conductive element may be a sheet metal connector. The sheet metal connector may have at least one tapered end for breaking when the force of the tool is applied. The sheet metal connector is configured to have breakpoints for breaking when the force of the tool is applied.

In accordance with an additional inventive facet, a method is performed by a processor on a printed circuit board of an on-body medicament delivery device for delivering medicament to a user. The printed circuit board contains at least a portion of an electrical circuit for powering an alarm. The method entails triggering the alarm to vibrate and/or make a noise. Per the method, responsive to either detection of removal of the medicament delivery device from the user or mechanical manipulation of a component of the medicament delivery device, shutting off the alarm without harming the printed circuit board.

The medicament delivery device may contain capacitive sensing electrodes, and the detecting that the medicament delivery device has been removed from the user may be based on output from the capacitive sensing electrodes indicating that the medicament delivery device has been removed from the user. The component that has been mechanically manipulated may have been mechanically manipulated to mechanically decouple the alarm. The component that has been mechanically manipulated may be a knob that has been mechanically manipulated by being rotated.

BRIEF DESCRIPTION OF THE DRAWINGS

FIG. 2A depicts illustrative components of a medicament delivery device of exemplary embodiments.

DETAILED DESCRIPTION

Figure 1A:
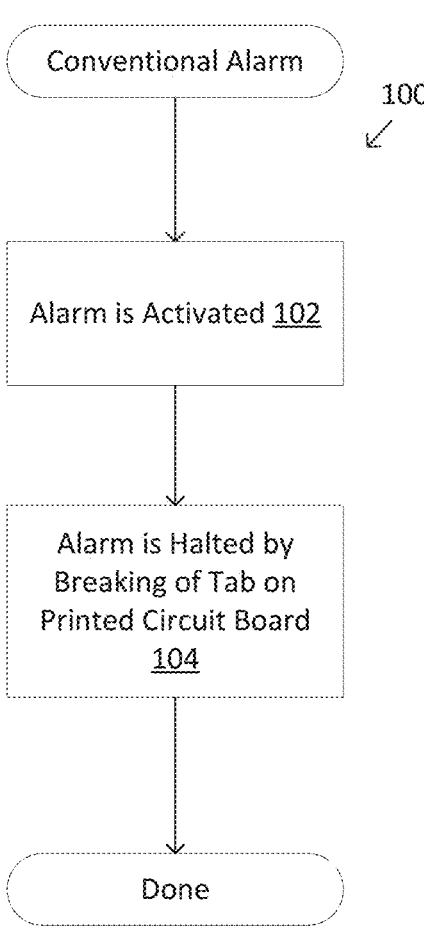
FIG. 1A depicts a flowchart of steps performed by a conventional medicament delivery device to shut off an alarm.
Figure 1B:
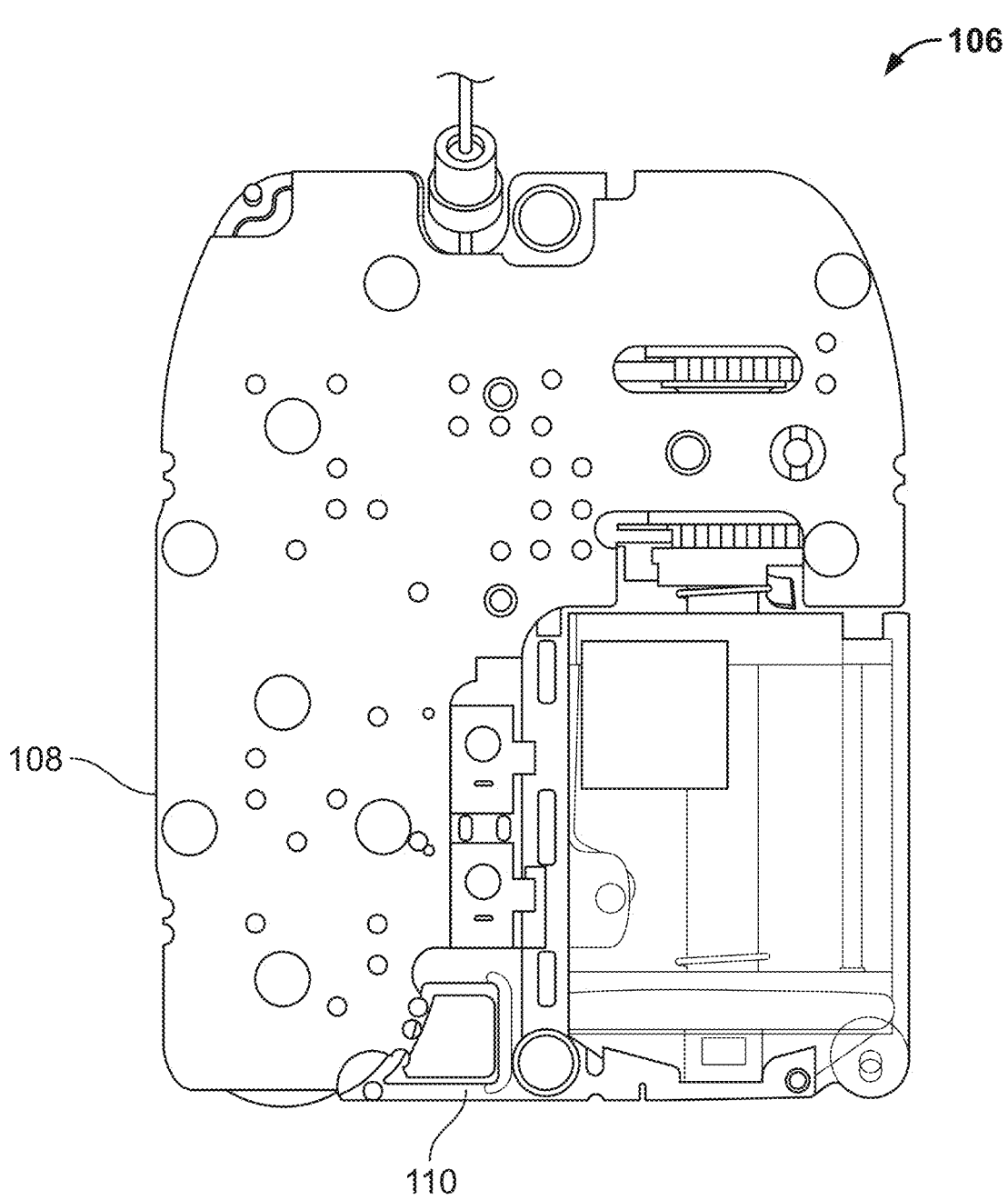
FIG. 1B depicts internal components of a conventional medicament delivery device.

The exemplary embodiments may provide approaches and components for shutting off an alarm of a medicament delivery device without harming the internal PCBA of the medicament delivery device. As a result, the PCBAs of medicament delivery devices may not be damaged and can be harvested for reuse in other incarnations of the medicament delivery devices.

Some exemplary embodiments may provide a displaceable component that may be displaced to open an electrical circuit that powers an alarm of the medicament delivery device. The displaceable component may be connected to an electrically conductive element or include such an electrically conductive element in some exemplary embodiments. In other exemplary embodiments, the displaceable component is the electrically conductive element.

In still other exemplary embodiments, the electrically conductive element is breakable. To shut off the alarm, a user breaks the electrically conductive element, such as by applying sufficient force with a tool. The tool may be, for example, a paper clip or pin.

In additional exemplary embodiments, the alarm may be shut off by mechanical manipulation of the medicament delivery device. For example, in some exemplary embodiments, a knob may be turned to shut off the alarm. The turning of the knob may mechanically isolate or decouple the alarm. In other exemplary embodiments, capacitance sensing electrodes may be used to sense removal form the skin of the user and turn off the alarm in response.

FIG. 2A depicts an illustrative medicament delivery device 200 for exemplary embodiments. The medicament delivery device 200 may deliver a medicament held in reservoir 202 to a user. A pump 204 pumps the medicament out of the reservoir 202 to the user. A cannula 206 is used to pierce the skin of the user and deliver the medicament that is pumped out of the reservoir 202 to the user. A processor 208, such as a central processing unit (CPU), graphics processing unit (GPU), application specific integrated circuit (ASIC), field programmable gate array (FPGA), or the like, may be provided. The processor 208 may execute computer programming instructions 212 stored in a storage 210 to control operation of the medicament delivery device 200. The storage 210 may also hold data 214. The storage 210 may be a non-transitory computer-readable storage medium. The storage may include random access memory (RAM), read only memory (ROM), solid state memory, magnetic disk memory, optical disk memory or combinations thereof.

Figure 2B:
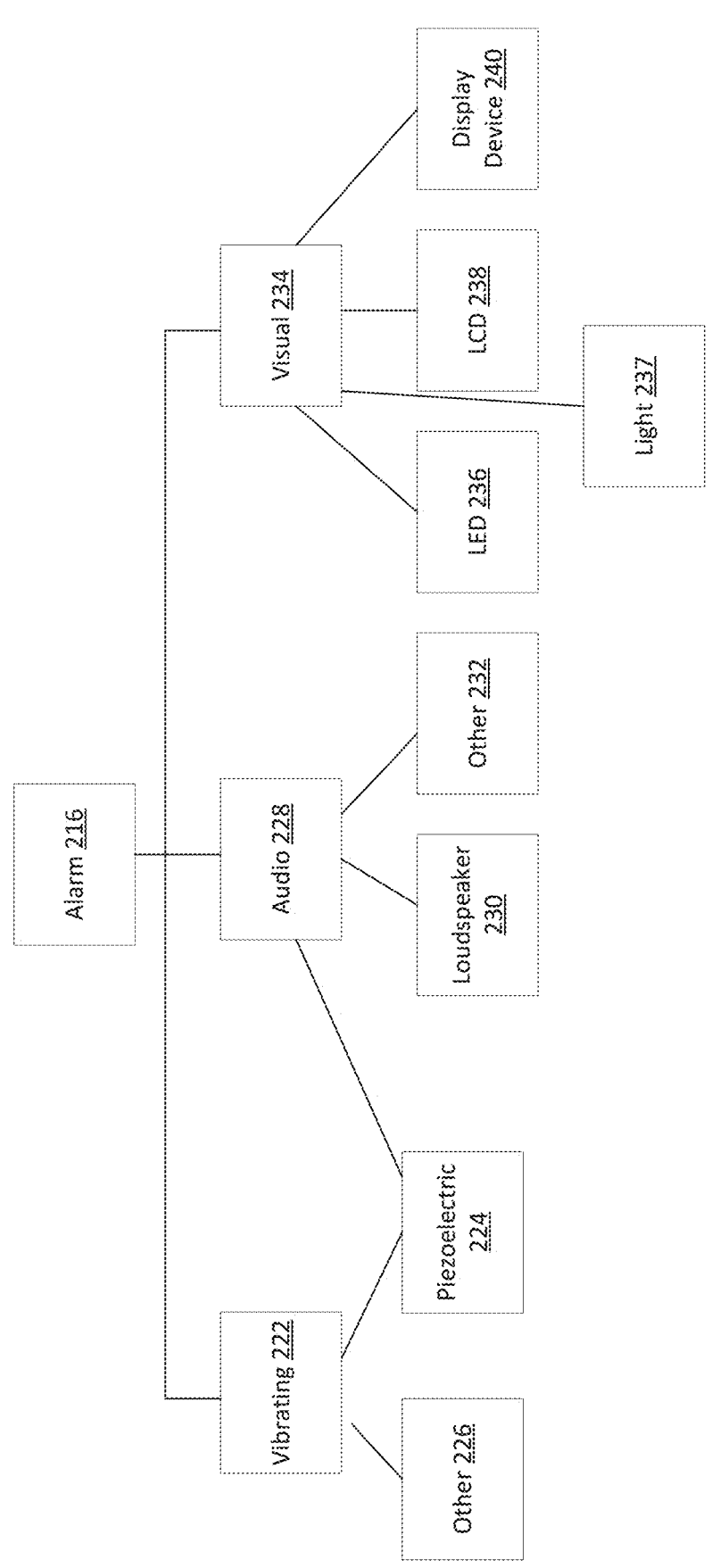
FIG. 2B depicts a diagram of illustrative types of alarms that may be used in exemplary embodiments.

The medicament delivery device 200 may include an alarm 216. The alarm 216 may be triggered by a number of different conditions or events that require the attention of the user. The alarm 216 may take may different forms, as shown in FIG. 2B. In some exemplary embodiments, the alarm 216 may be a vibrating alarm 222 or may be an audio alarm 228. The vibrating alarm 222 may be a piezoelectric component 224 that vibrates in response to application of electricity or may be another type of vibrating device 226. The resulting vibration may serve as the alarm 216 or may be only part of the alarm to the user, which may include audio and/or visual output as well. In other instances, the piezoelectric component 224 may cause a sound to be generated. For example, the piezoelectric component 224 may be secured to a housing of the medicament delivery device 200 to cause an audio output when the piezoelectric component 224 vibrates. Still further, in other embodiments, the audio alarm 228 is a loudspeaker 230 or another variety audio output device 232. Moreover, in some embodiments, the alarm may include a visual alarm 234, such as a light emitting diode (LED) 236, a light 237, a liquid crystal display (LCD) 238, or other type of display device 240.

Figure 2C:
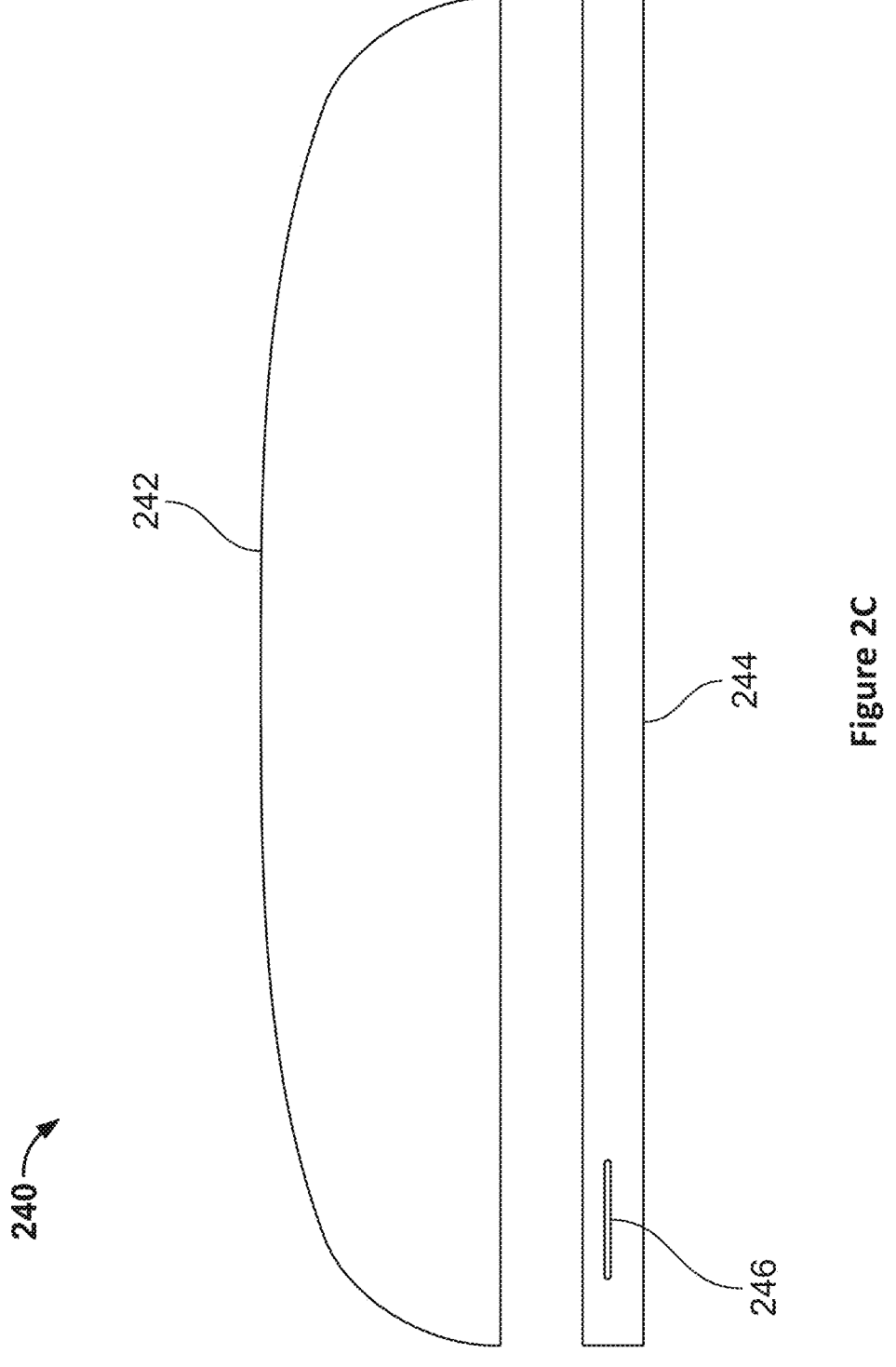
FIG. 2C depicts an illustrative arrangement of an alarm in a bottom housing in exemplary embodiments.

FIG. 2C shows a partially exploded side view of the housing 240 of the medicament delivery device 200. The housing 240 may include an upper housing 242 and a lower housing 244. The upper housing 242 and the lower housing 244 may be secured by a snap fit, screws or other connection mechanism. In this instance, the alarm 216 is a piezoelectric component 246 that is positioned in the lower housing 246, or is secure to the lower housing 244 or in close proximity to the lower housing 244.

As shown in FIG. 2A, the power for the alarm 216 may originate from a power source 218. In exemplary embodiments the power source 218 may comprise one or more batteries. The batteries may be, for example, button cell batteries, rechargeable batteries or other suitable batteries. The power source 218 may be a charged capacitor is some exemplary embodiments.

Figure 3:
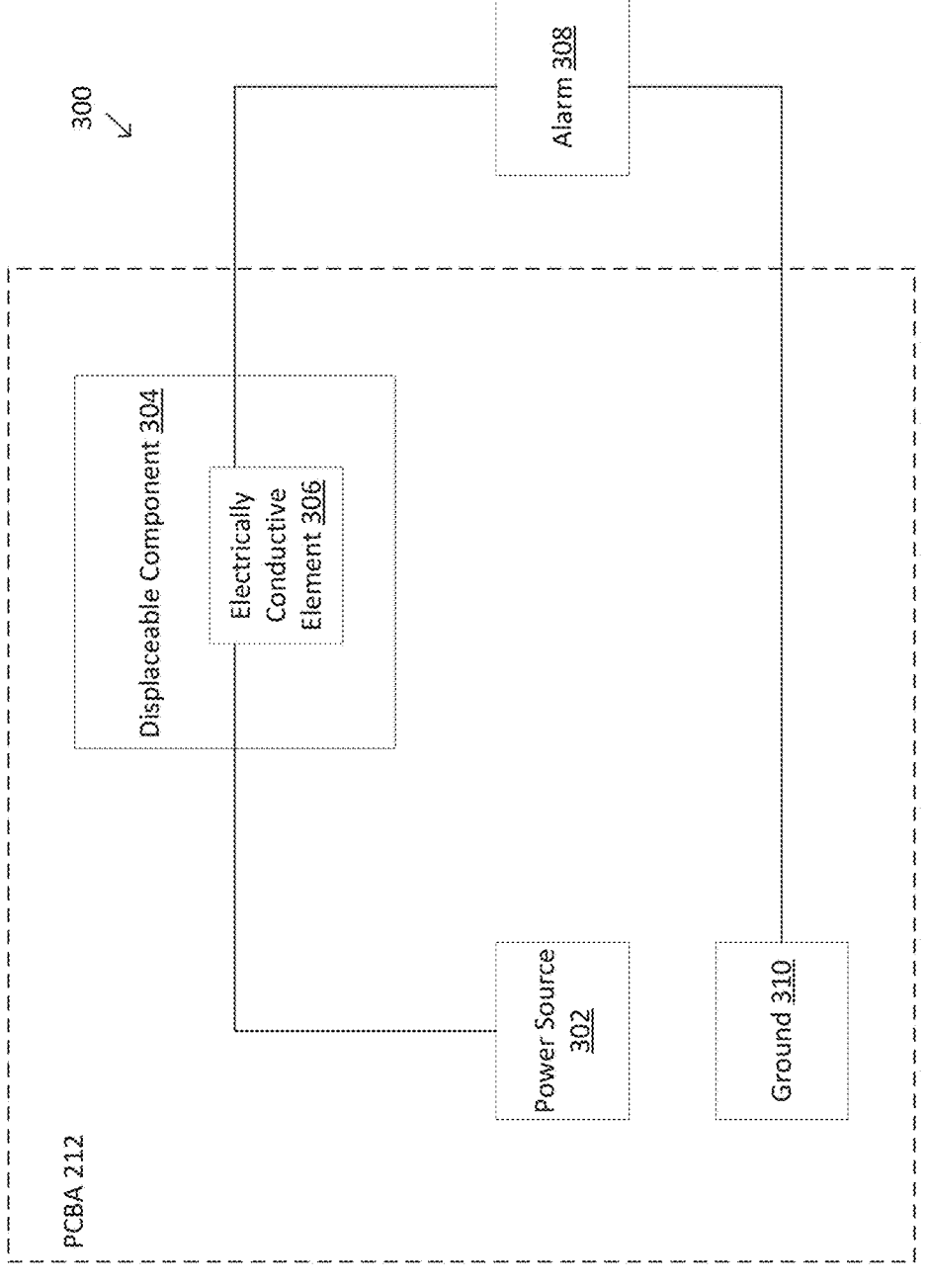
FIG. 3 depicts an illustrative electrical circuit of exemplary embodiments for powering an alarm where the electrical circuit includes a displaceable component with an electrically conductive element.

FIG. 3 depicts an illustrative electrical circuit 300 for providing power to the alarm 308. The power source 302 is electrically connected with an electrically conductive element 306. The electrically conductive element 306 may take many forms as described below. The electrically conductive element 36 may be part of or connected to displaceable component 304. In some embodiments, the electrically conductive element 306 is the displaceable component 304. The displaceable component 304 is displaceable so that the electrical connection with the other components in the electrical circuit 300 is broken and the electrical circuit becomes open so that no current flows through the electrical circuit 300. The electrically conductive element 306 electrically connects the power source with the alarm 308. The current in the electrical circuit 300 flows to ground 310 when the circuit 300 is closed. The power source 302, electrically conductive element 306 and ground may be found on an internal PCBA 312 in some embodiments.

Figure 4:
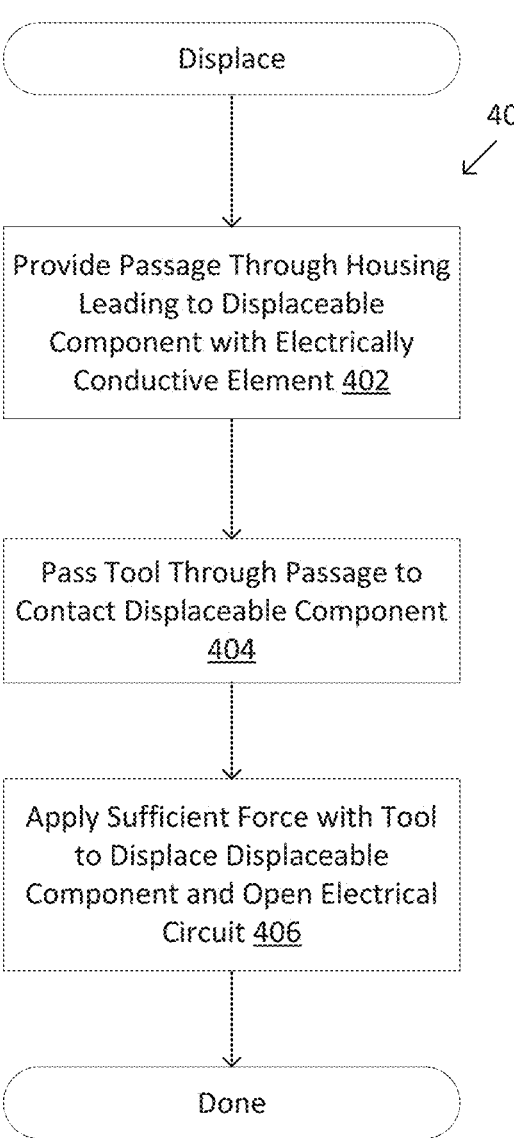
FIG. 4 depicts a flowchart of illustrative steps that may be performed in exemplary embodiments to shut off the alarm by displacement.

FIG. 4 depicts a flowchart 400 of illustrative steps that may be performed in exemplary embodiments to disable alarm 216 of the medicament delivery device 200 by displacing the displaceable component 304 and the electrically conductive element 306 so as to open the electrical circuit 300 that powers the alarm 308. At 402, a passage is provided in the medicament delivery device 200. The passage leads to the electrically conductive element 306. Different options for the electrically conductive element 306 found in exemplary embodiments are described below. At 404, the passage is adapted to accept a tool so that the tool may make contact with the displaceable component 304. Thus, the passage is sized and shaped to accommodate the tool being inserted into a sufficient length of the passage so as to contact the displaceable component 304. At 406, sufficient force is applied by the tool to the displaceable component 304 so as to displace the displaceable component 304 and open the electrical circuit 300. The tool may move the displaceable component 304 so that the electrically conductive component 306 is no longer electrical connected to the electrical component. The displaceable component 304 may be simply moved or may be deformed, such as by being bent, so that the electrically conductive component 306 is no longer electrically connected to the electrical circuit 300.

Figure 5A:
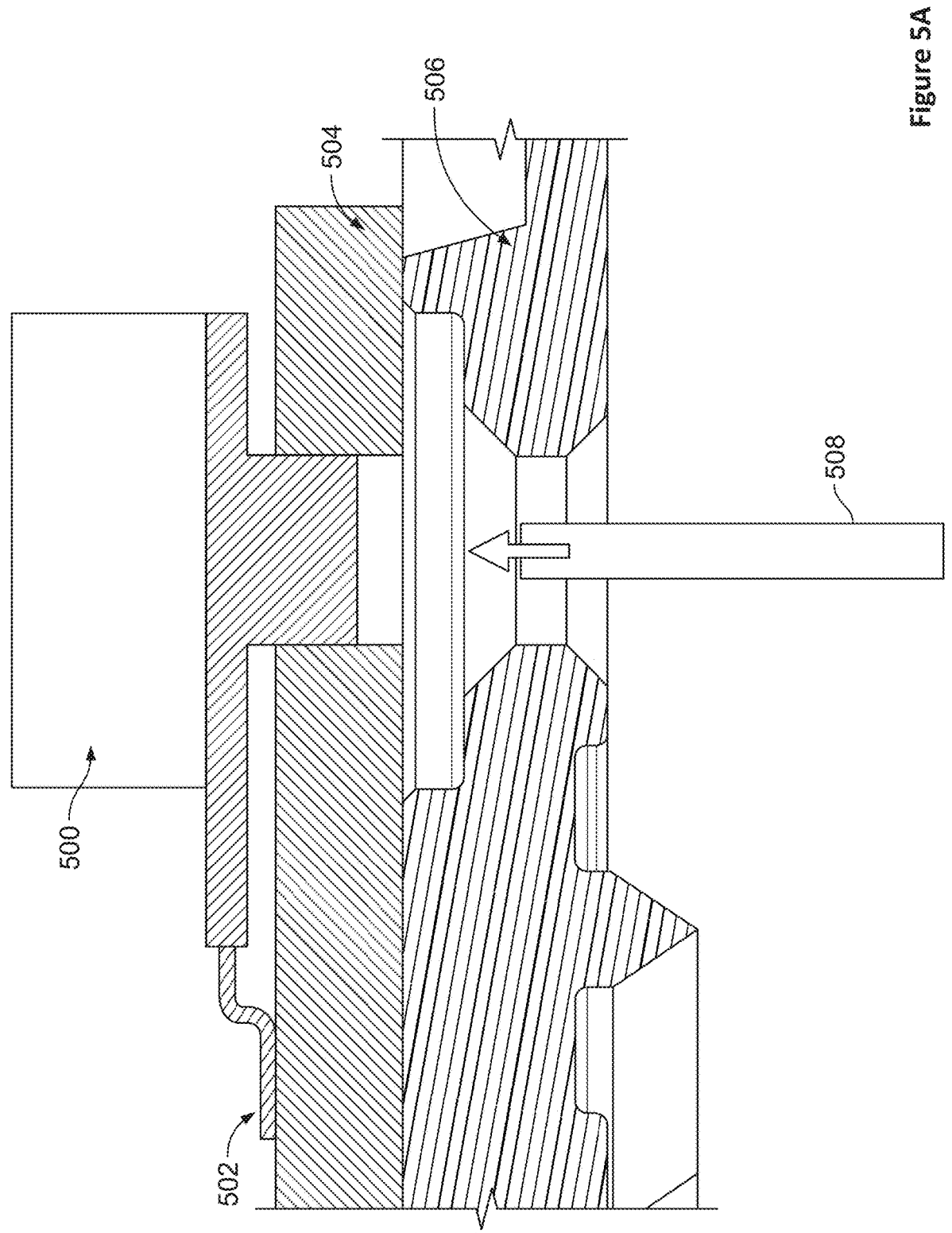
FIGS. 5A, 5B, and 5C depict a first exemplary embodiment that shuts off the alarm using displacement.

FIG. 5A depicts a first exemplary embodiment of a configuration for disabling alarm 216 of the medicament delivery device 200 without harming a PCBA of the medicament delivery device 200. In this first exemplary embodiment, a compliant mechanism 500 is positioned in a through hole that serves as a passage for a tool 508, such as a paper clip or pin. The passage passes through the bottom housing 244 of the medicament delivery device 200. In this embodiment, the displaceable component 304 is the compliant mechanism 500. An electrically conductive surface contact 504 is secured to the complaint mechanism 500. The surface contact 502 may be made of an electrically conductive metal, such as copper, and is in physical contact with an electrical contact on a printed circuit board (PCBA) 504. The PCBA 504 may hold electrical components of the medicament delivery device, like processor 208, storage 210, power source 218 and the like. A portion of the electrical circuit 300 that powers the alarm 308 may be present on the PCBA 504, and may include the surface contact 502 and the contact on the PCBA 504 that is in electrical and physical contact with the surface contact 502. In this first embodiment, the surface contact 502 acts as the electrically conductive element 306. The passage extends through the bottom housing 506 to the compliant mechanism 500.

Figure 5B:
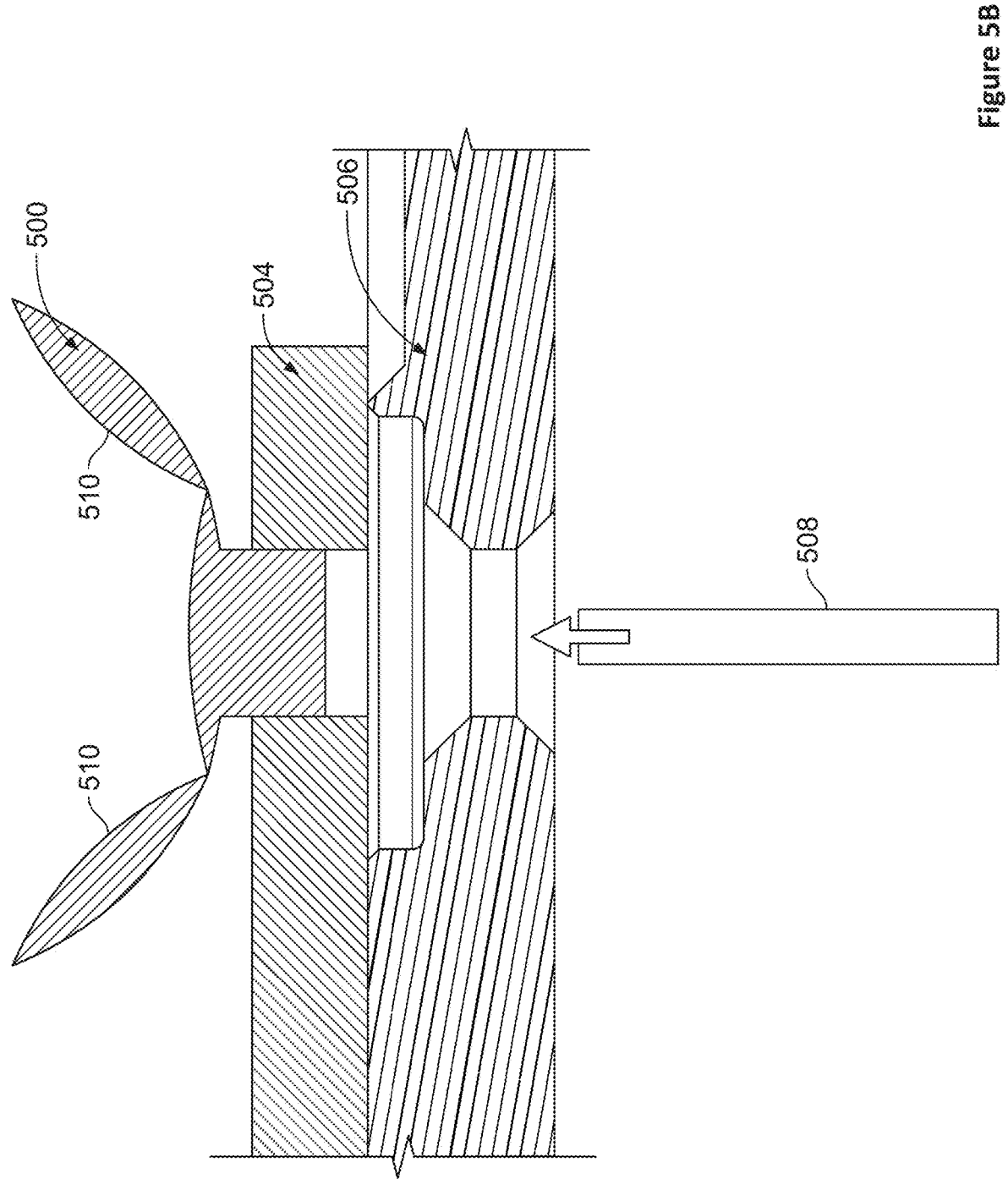
Figure 5C:
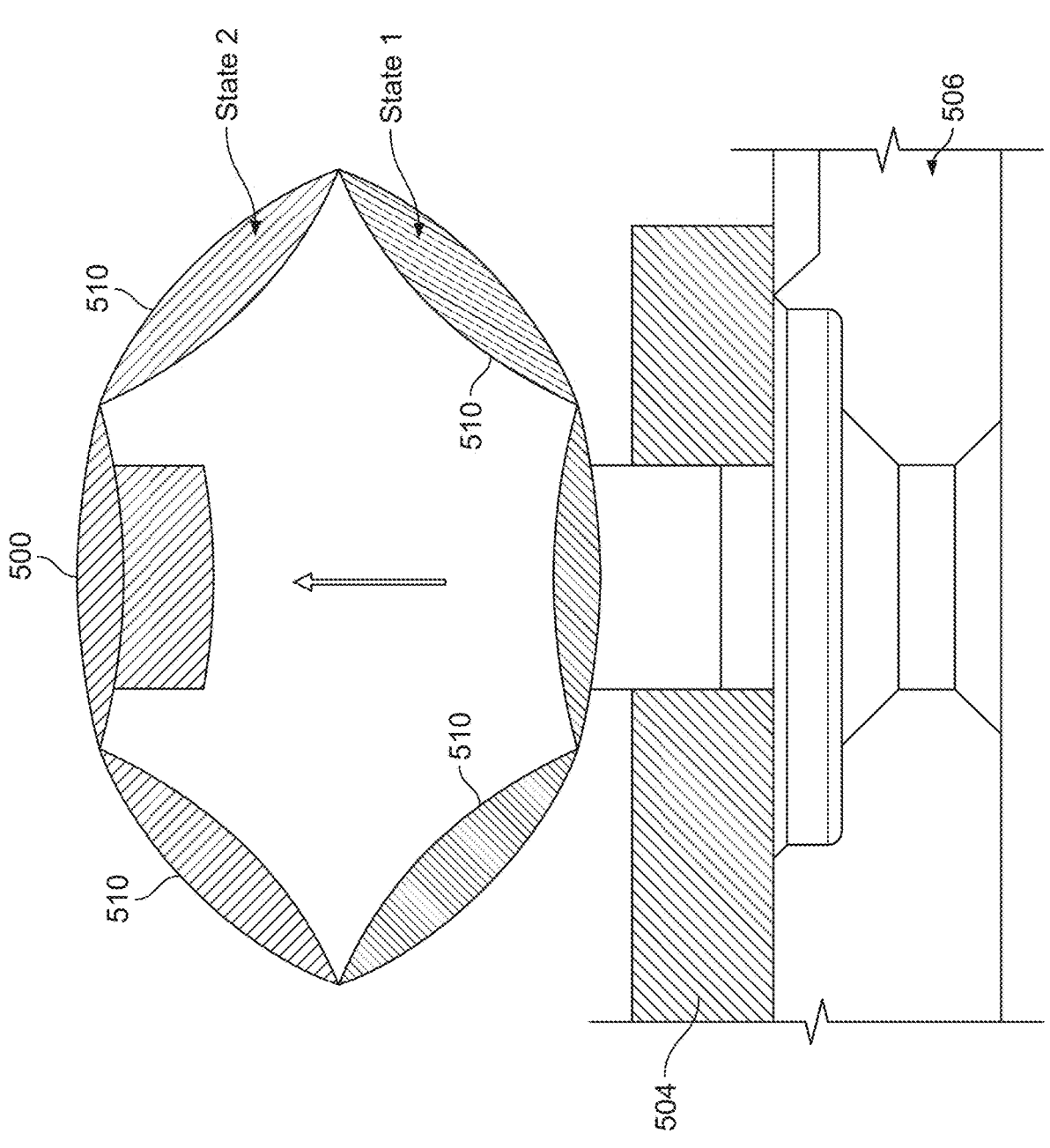

As shown in FIG. 5B the compliant mechanism may be initially in the state shown with the wing elements 510 in an upward orientation before the tool 508 applies force to the compliant mechanism. The tool 508 may be pushed upward through the passage that extends through the bottom housing 506 to contact the compliant mechanism 500 and apply sufficient mechanism to cause the compliant mechanism to be displaced and deformed to a new state with the wing elements 510 transform from the downward facing orientation (i.e., State 1) to face downward (i.e., State 2) as shown in FIG. 5C, where plug 512 is displaced out of the passage. The result is that the surface contact 502 is displaced and no longer is in contact with the PCBA 504. Hence, there no longer is an electrical connection with the contact on the PCBA 504, and the electrical circuit 300 is open. The alarm 216 shuts off as a result without harming the PCBA 504.

Figure 6A:
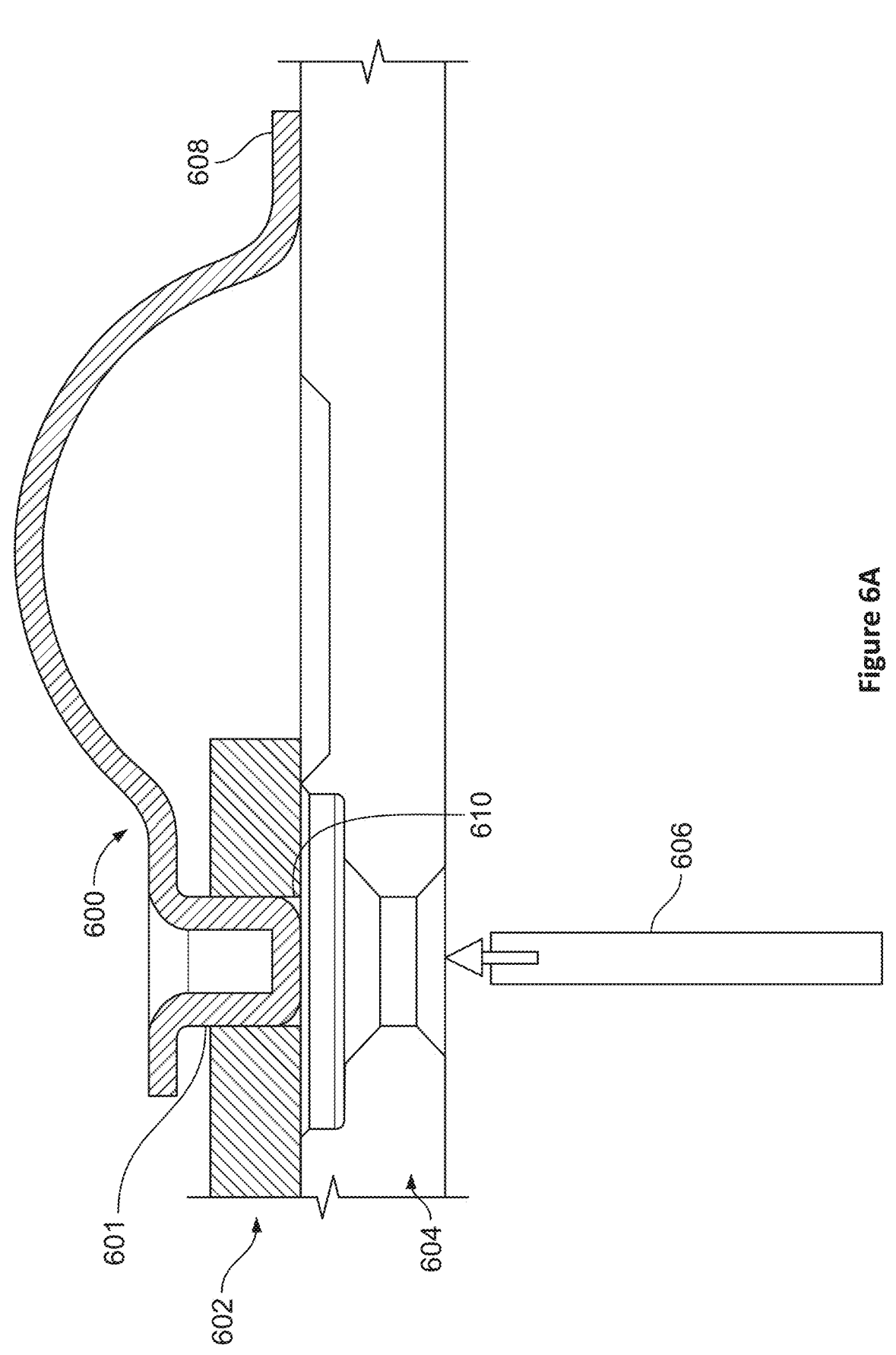
FIGS. 6A and 6B depict a second exemplary embodiment that shuts off the alarm using displacement.
Figure 6B:
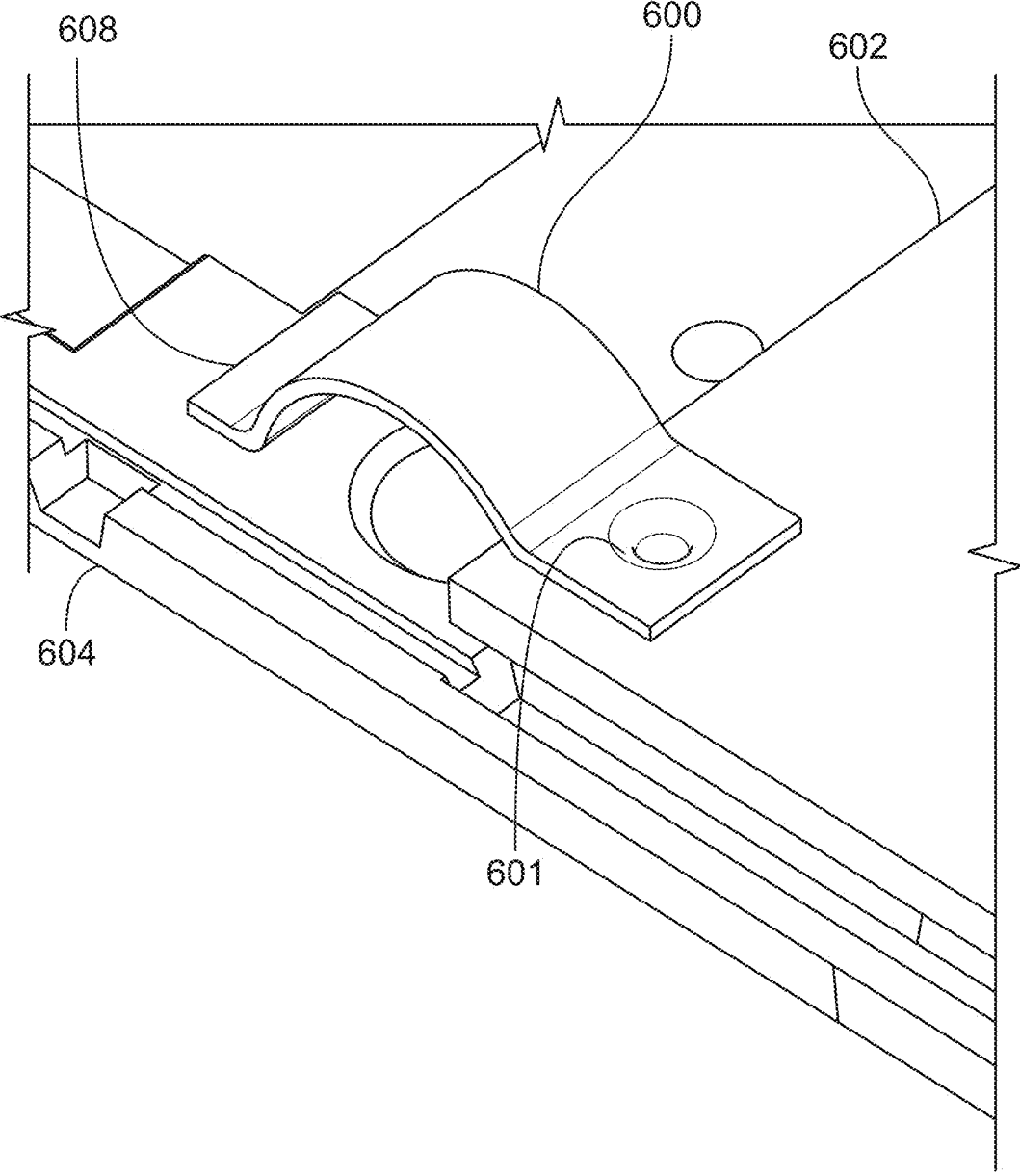

FIGS. 6A and 6B depict a second exemplary embodiment. In this second exemplary embodiment, a sheet metal clip 600 is the electrically conductive element 306 that also acts as the displaceable component 304. The sheet metal clip 600 has a formed feature 601 that fits into a plated through hole 610. The plated through hole 610 passes through PCBA 602. The feature 601 is structured to be biased outward and create a friction fit with the wall of the plated through hole 610. The contact between the feature 601 and the walls of the plated through hole 610 creates an electrical connection to close the electrical circuit 300. End 608 of the sheet metal clip 608 may be secured to the bottom housing 604 surface. When the tool 606 is pushed upward through the passage with sufficient force, the feature 601 is displaced out of the plated through hole 610 and the electrical connection is broken so that the electrical circuit 300 becomes open.

Figure 6C:
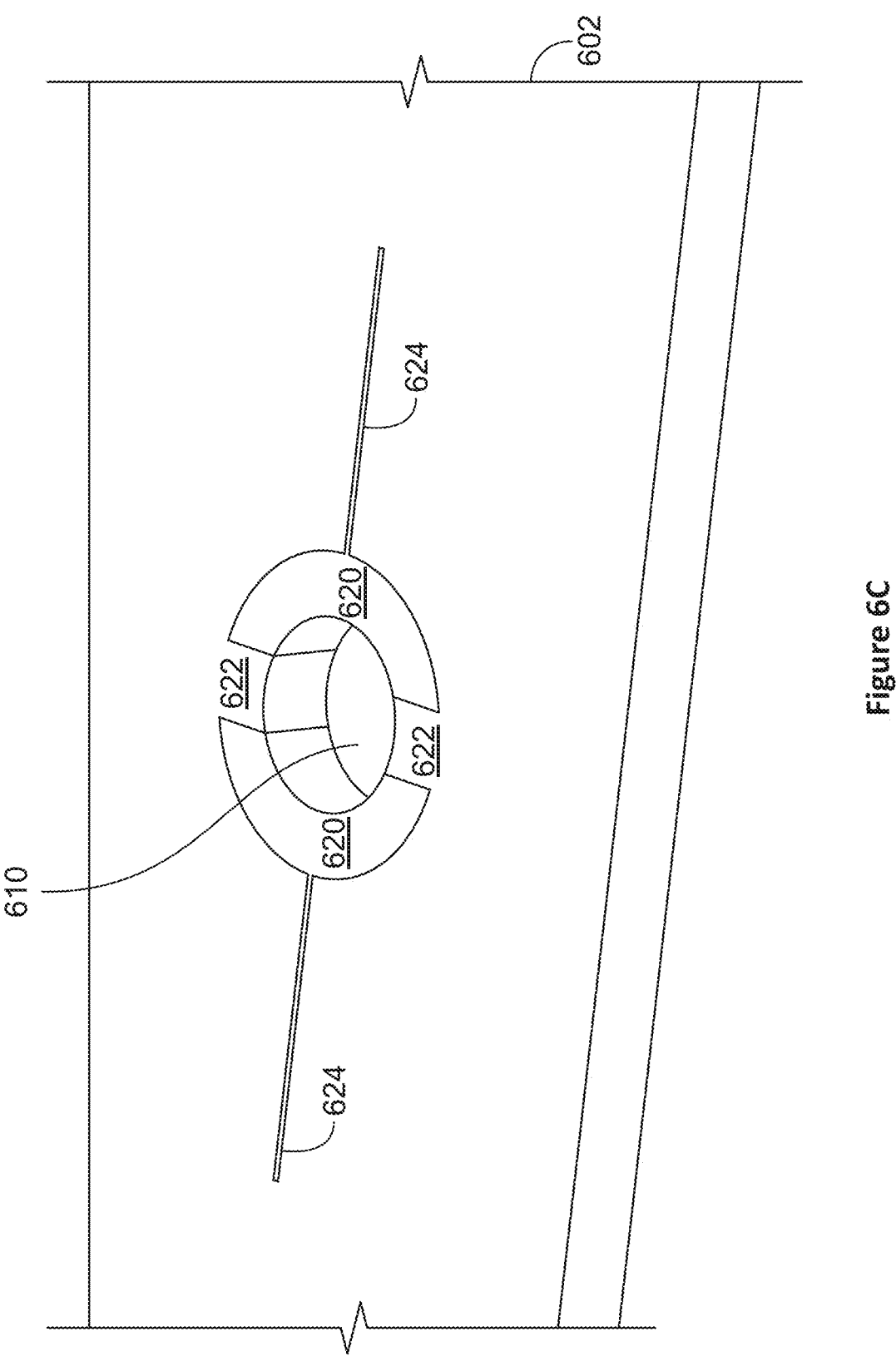
FIGS. 6C and 6D depict illustrative at least partially plated through holes designs for the exemplary embodiments.

FIG. 6C shows one example design for the plated hole 610 that may be used in the embodiment of FIGS. 6A and 6B. As can be seen in FIG. 6C, the plated through hole is not completely plated around the circumference of the hole 610 but rather is only plated partially around the circumference of the hole 610. There are semicircular regions 620 of plating separated by non-plated gaps 622 on the PCBA 602. Electrical traces 624 lead from the respective semi-circular regions 620. The feature 601 completes the electrical circuit when the feature 601 is in place in the plated through hole by being in physical and electrical contact with the plated regions 620.

Figure 6D:
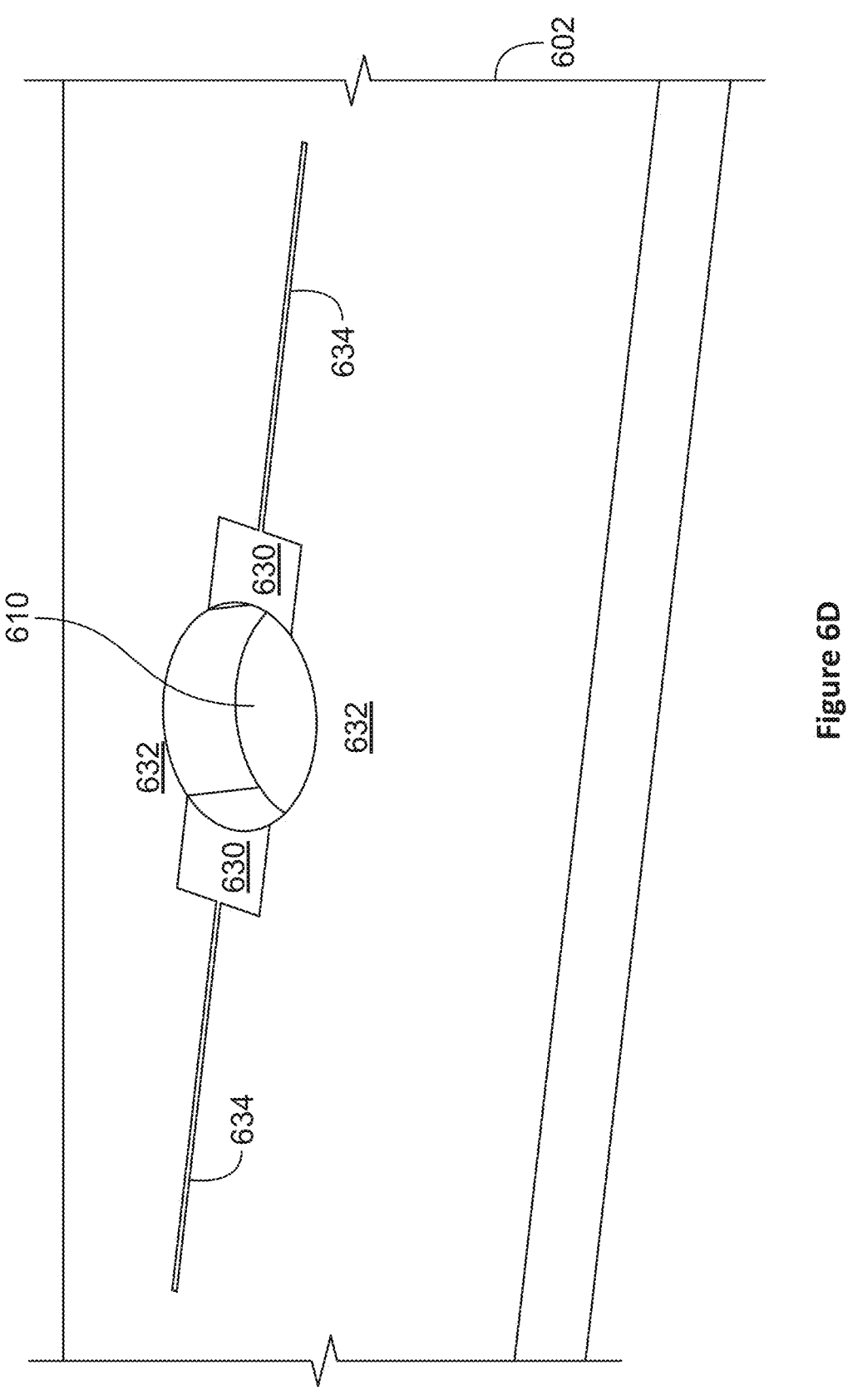

FIG. 6D shows another example design for the plated through hole 610 that may be used with the embodiment of FIGS. 6A and 6B. In this design, the plated through hole 610 has gaps 632 on the PCBA 602 that are not plated. The plated regions 630 are rectangular strips that extend through the hole 610 onto the surface of the PCBA 602. Electrical traces 634 lead from the respective the rectangular regions 630. The feature 601 completes the electrical circuit when the feature 601 is in place in the plated through hole by being in physical and electrical contact with the plated regions 630.

Figure 7A:
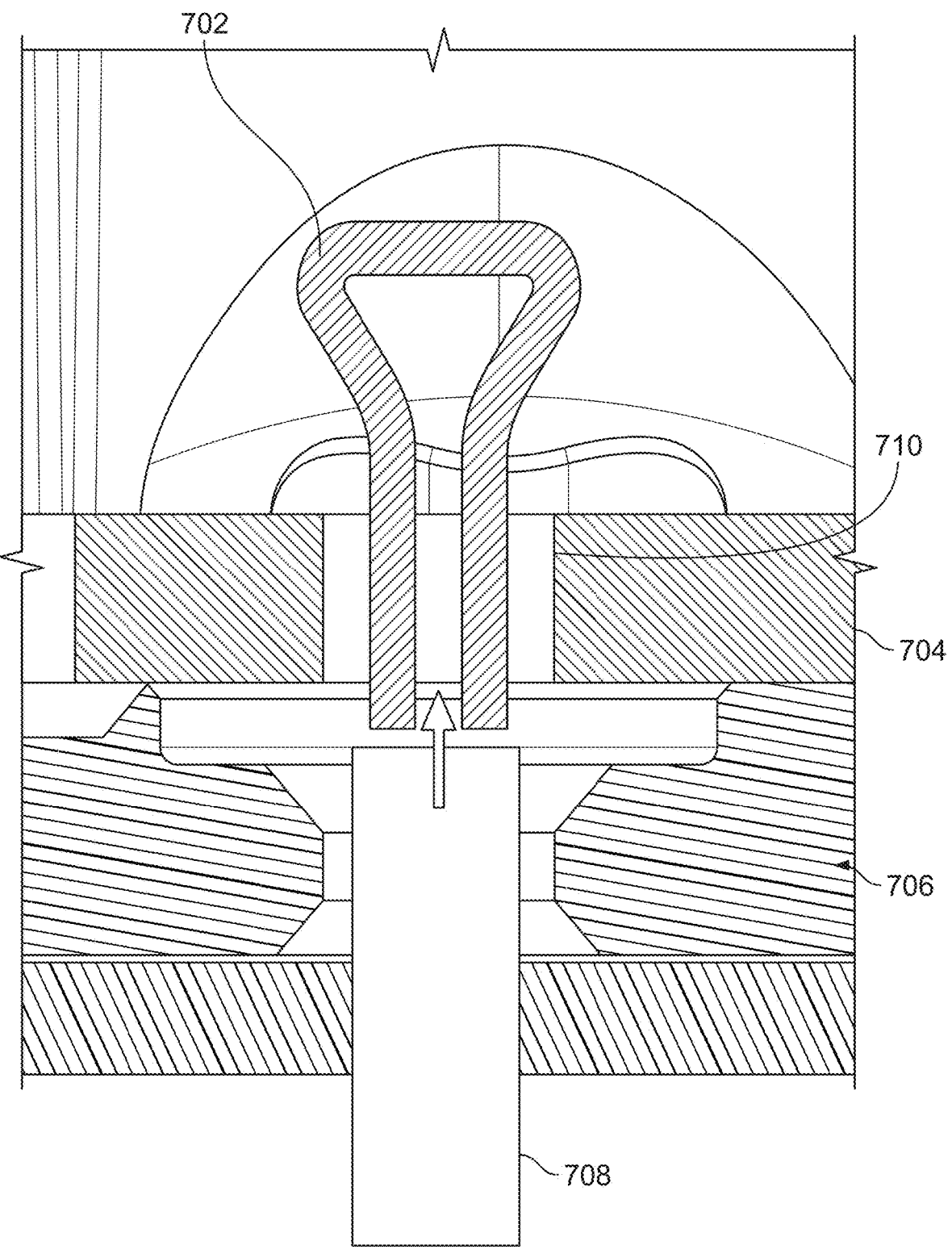
FIGS. 7A and 7B depict a third exemplary embodiment that shuts off the alarm using displacement.
Figure 7B:
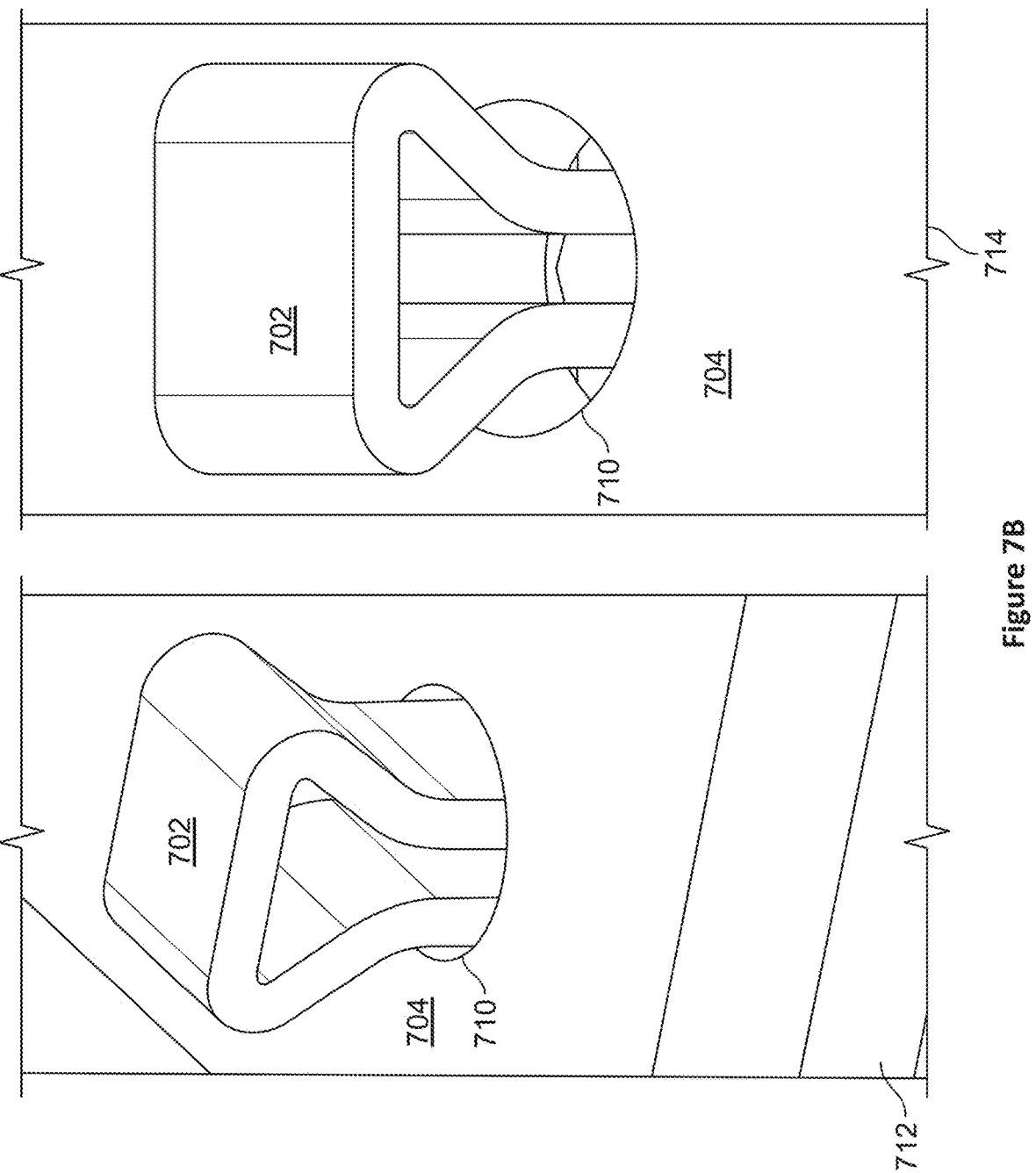

A third exemplary embodiment is depicted in FIGS. 7A and 7B. As can be seen in the two different perspectives 712 and 714 of FIG. 7B, a metal clip 702 is positioned in a plated through hole in PCBA 704. The clip 702 is biased outward so that the clip contact the plated walls of the through hole 710. The clip 702 serves as both the electrically conductive element 306 and the displaceable component 304 in this third exemplary embodiment. As shown in FIG. 7A, to disable the alarm 216, a user pushes the tool 708 upward in passage through the bottom housing 706 to contact pin 702 to displace the pin 702 from the plated through hole 710 and break the electrical connection for the electrical circuit 300 to shut off the alarm 216.

The partially plated through hole designs of FIGS. 6C and 6D may be used in the embodiment of FIGS. 7A and 7B.

Figure 8A:
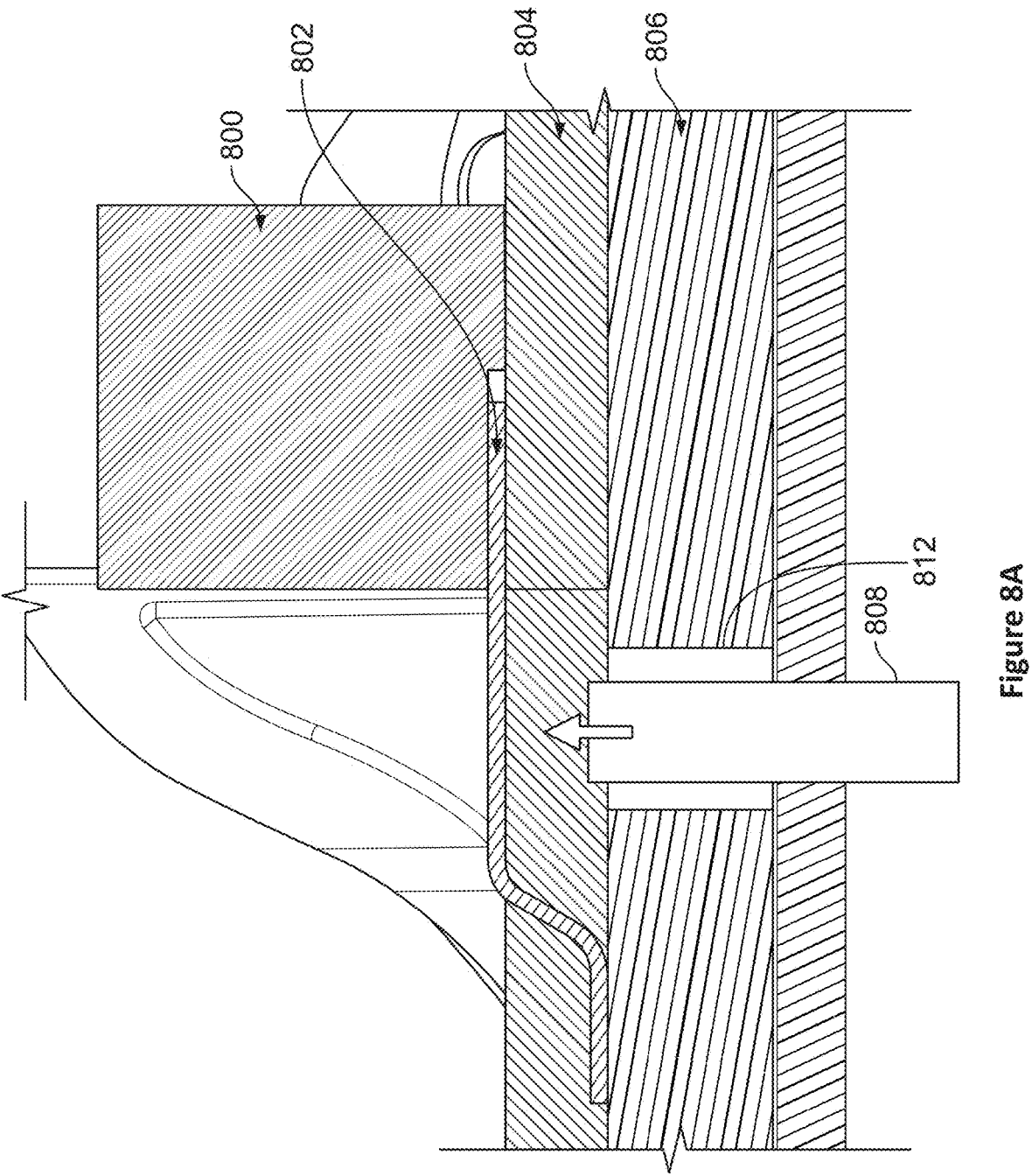
FIGS. 8A and 8B depict a fourth exemplary embodiment that shuts off the alarm using displacement.
Figure 8B:
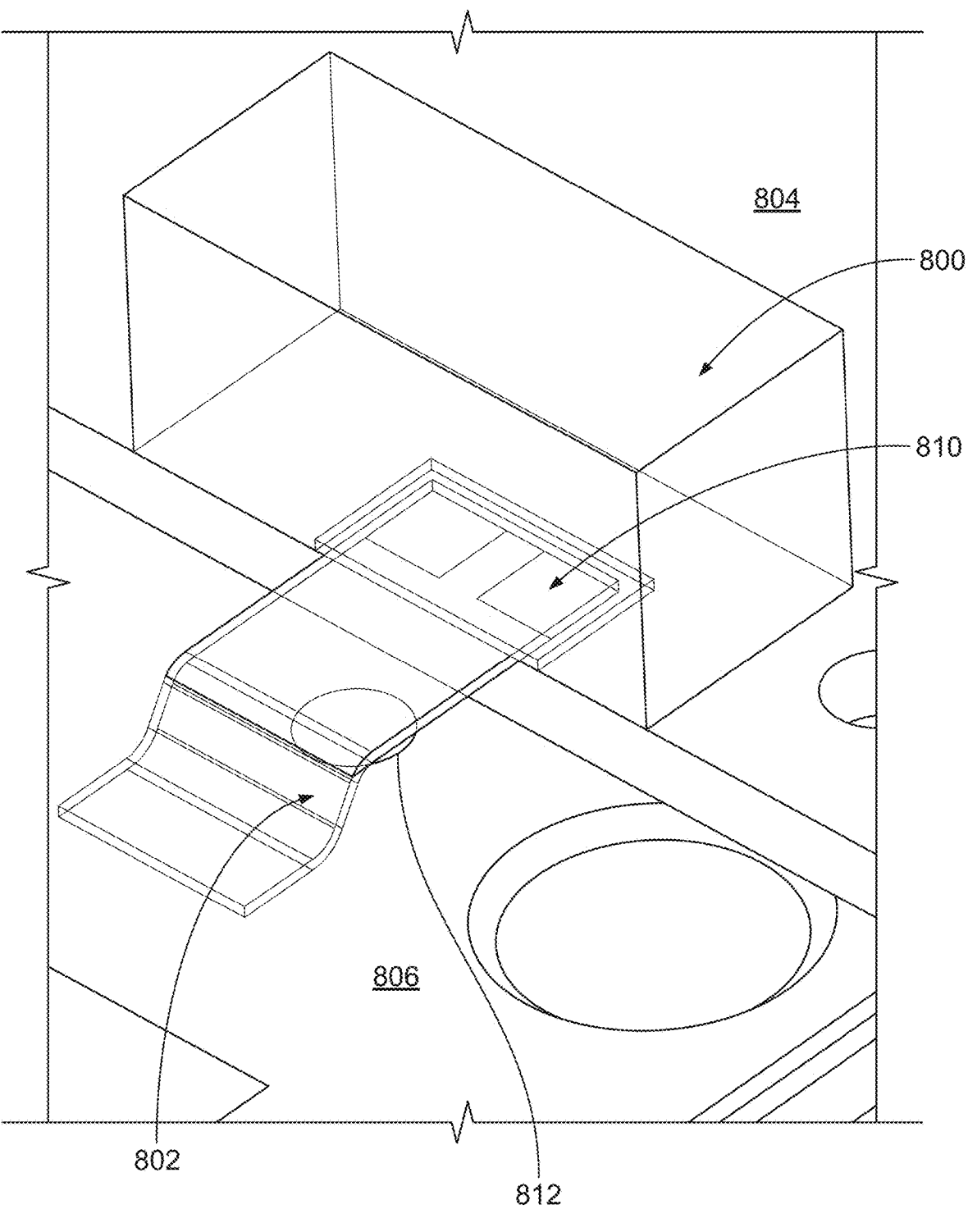

A fourth exemplary embodiment is shown in FIGS. 8A and 8B. In the fourth exemplary embodiment, a sheet metal clip 802 is mechanically and electrically connected to the bottom housing 806 of the medicament delivery device 200. The sheet metal clip 802 is pushed into electrical contact with plated component pads 810 on PCBA 804 by chassis 800 for the PCBA 804. The plated component pads 810 are part of the electrical circuit 300 that powers the alarm 216. The contact creates an electrical connection between the sheet metal clip 802 and the plated component pads 810. The sheet metal clip 802 serves as the displaceable component 304 and the electrically conductive component 306. When the tool 808 passes through the through hole 812 to contact the sheet metal clip 802 and apply sufficient force to deform and/or displace the sheet metal clip 802 so that the sheet metal tip becomes separated from the bottom housing 806 and to breaks the electrical connection with the electrical circuit 300. The breaking of the electrical connection shuts off the alarm 216.

It should be appreciated that other configurations than those depicted in the figures may be used to turn off the alarm by displacement. The configurations shown are intended to be illustrative.

Figure 9:
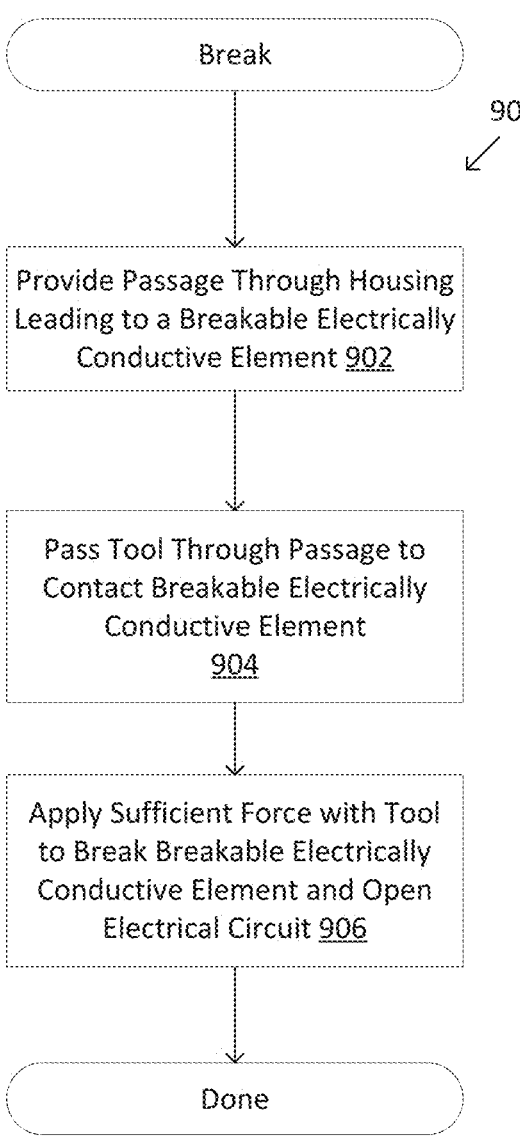
FIG. 9 depicts a flowchart of illustrative steps that may be performed in exemplary embodiments to shut off the alarm by breaking the electrically conductive element.
Figure 10:
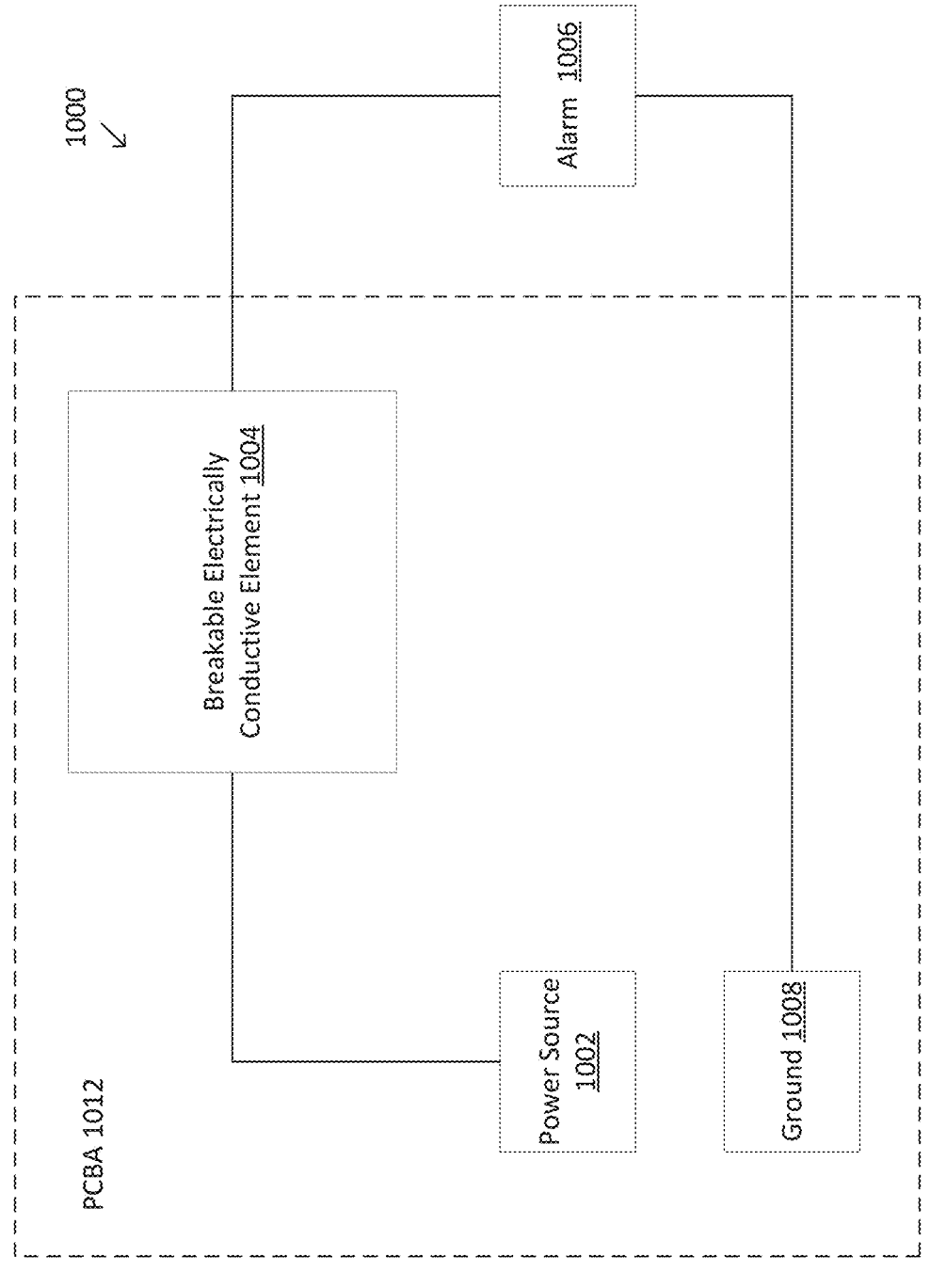
FIG. 10 depicts an illustrative electrical circuit of exemplary embodiments for powering an alarm where the electrical circuit includes a breakable electrically conductive element.

Another option to shutting off the alarm is to break the electrically conductive element that completes the electrical circuit that powers the alarm. FIG. 9 depicts a flowchart 900 of illustrative steps that may be performed in exemplary embodiments to shut off the alarm in exemplary embodiments by breaking the electrically conductive element. The flowchart 900 of FIG. 9 will be described with reference to the electrical circuit 1000 of FIG. 10, where a power source 1002, such as batteries or a charged capacitor, provide power to the alarm 1006. A breakable electrically conductive element 1004 is positioned in the circuit between the power source 1002 and the alarm. The current passes through the alarm 1006 to ground 1008. The power source 1002, the breakable electrically conductive element 1004, and the ground 1008 may be found on PCBA 1012 in some embodiments.

With reference to FIG. 9, at 902, a passage is provided through the housing leading to the breakable electrically conductive element 1004. At 904, the tool is passed through the passage to contact the breakable electrically conductive element 1004. At 906, sufficient force is applied by the tool to break the breakable electrically conductive element 1004. This causes the electrical circuit 1000 to become open so that the alarm 1006 shuts off due to lack of power.

Figure 11A:
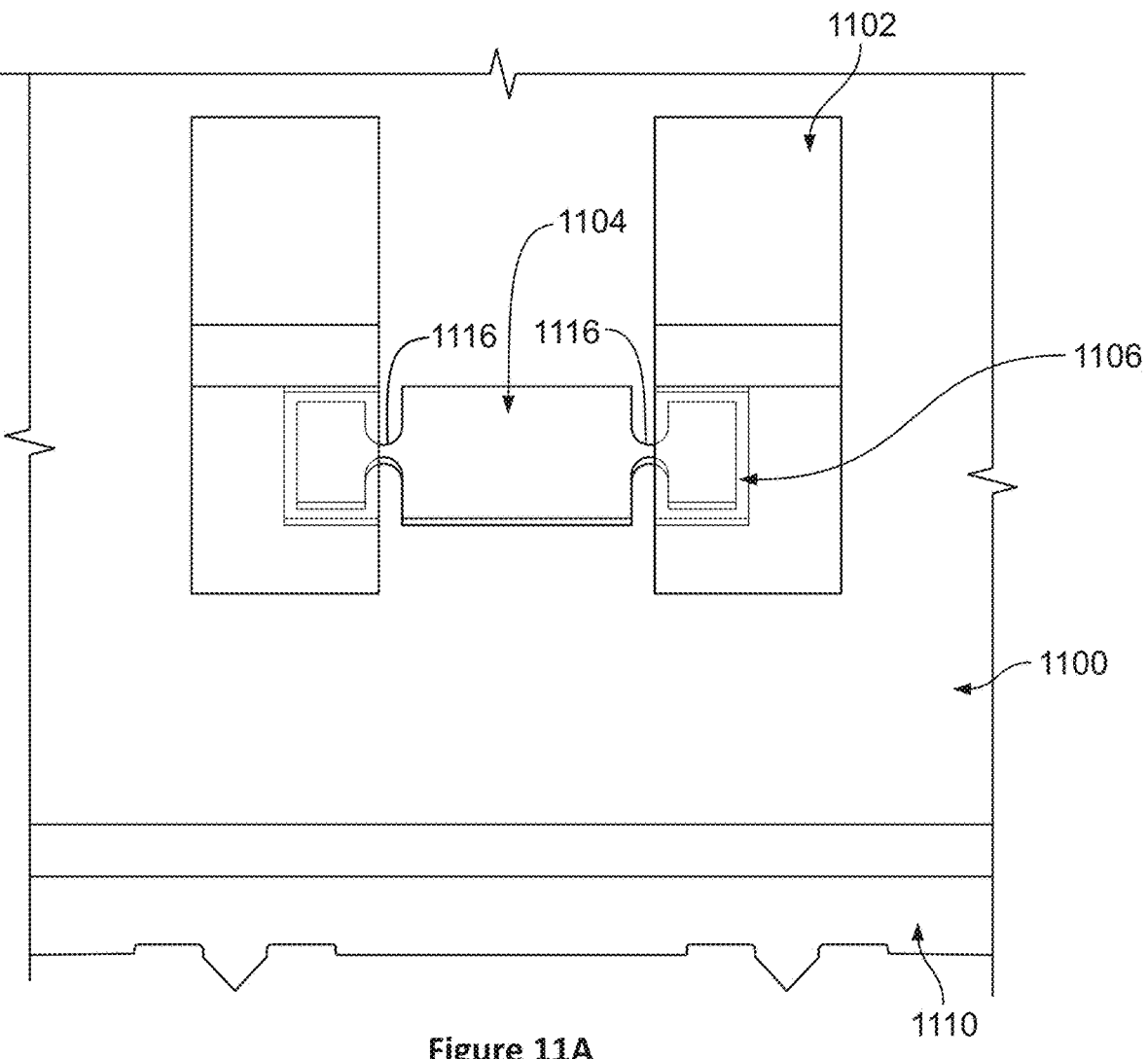
FIGS. 11A and 11B depict a fifth exemplary embodiment that shuts off the alarm by breaking the electrically conductive element.
Figure 11B:
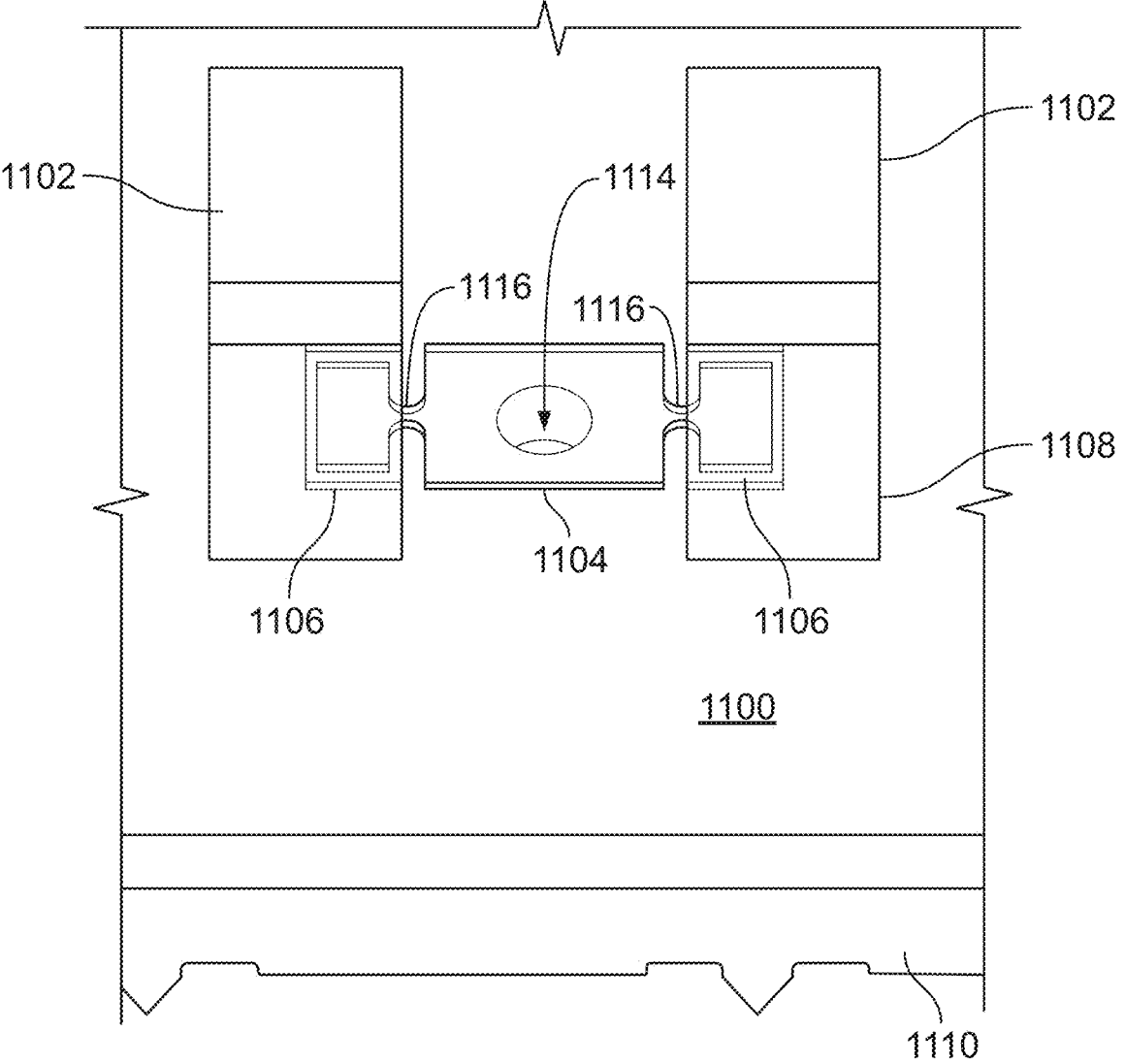

FIGS. 11A and 11B depict an illustrative fifth exemplary embodiment that relies on breaking the breakable conductive element 1004 to shut off the alarm 1006. Component pads 1106 are provided on PCBA 1104. These component pads 1106 are part of the electrical circuit 1000 that powers the alarm 1106. A sheet metal conductor 1104 is in contact with the component pads to complete the electrical connection with the component pads 1106. The chassis presses the sheet metal connector 1104 into secure contact with the component pads 1104. The sheet metal connector 1104 is the breakable electrically conductive element 1004 in this exemplary embodiment. The sheet metal connector has thin tapered necks 1116 near both component pads 1106. These necks 1116 are designed to be breakpoints when sufficient force is applied to the sheet metal connector 1104. Specifically, when tool passes into through the bottom housing 1110 via through hole 1114 to apply sufficient force to the underside of the sheet metal conductor, one or more of the necks 1116 break to open the electrical circuit 1000 and shut off the alarm 1006.

It should be appreciated that other breakable electrical connector arrangements may be used. The depiction in FIGS. 11A and 11B is illustrative.

Figure 12:
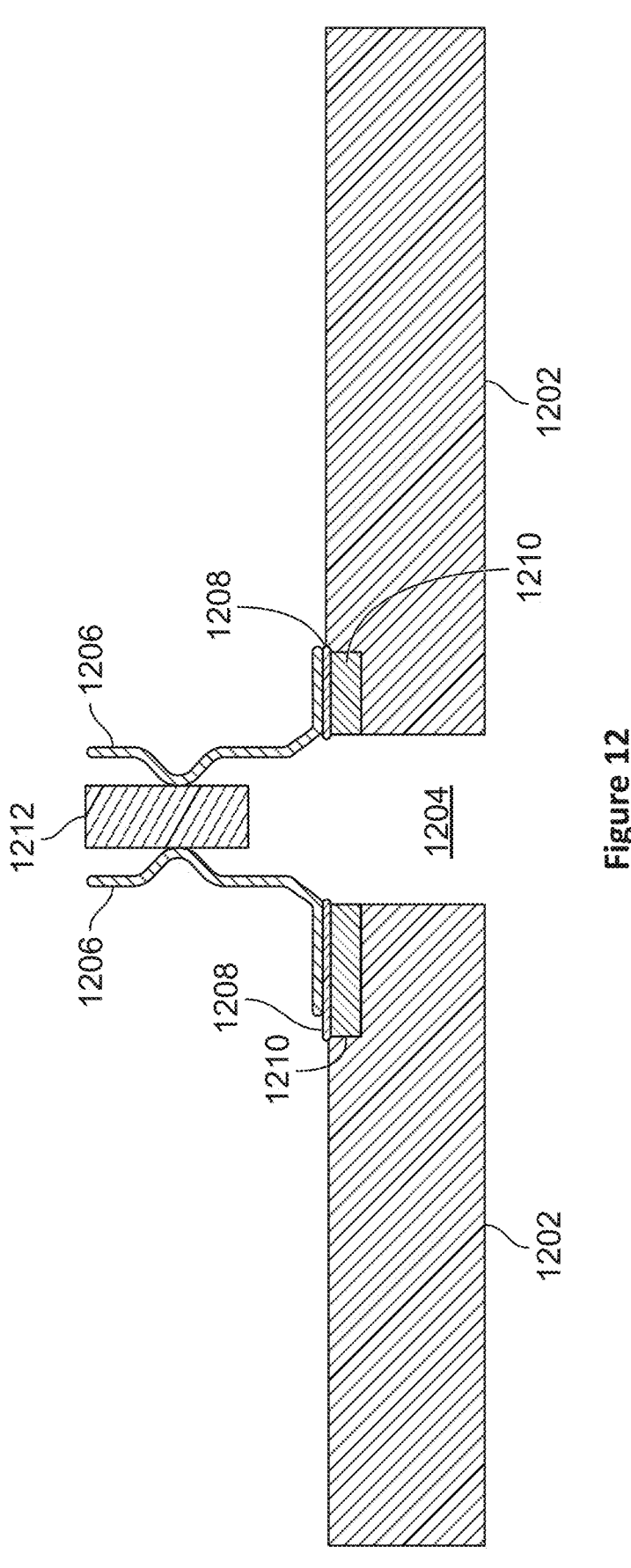
FIG. 12 depict a sixth exemplary embodiment that shuts off the alarm using displacement.

FIG. 12 depicts a sixth exemplary embodiment wherein the electrically conductive element is not secured to the PCBA 1202, rather the electrically conductive element 1212 is held captive above the PCBA 1202 by electrically conductive spring clips 1206. The spring clips 1208 are secured to electrically conductive elements 1210 on the PCBA 1202 via electrically conductive solder. The elements 1206, 1208, 1210 and 1212 are part of electrical circuit that powers the alarm. To disable the alarm 216, a tool passes up via through hole 2104 to displace the element 1212 from between the spring clips 1206 and open the electrical circuit.

Figure 13:
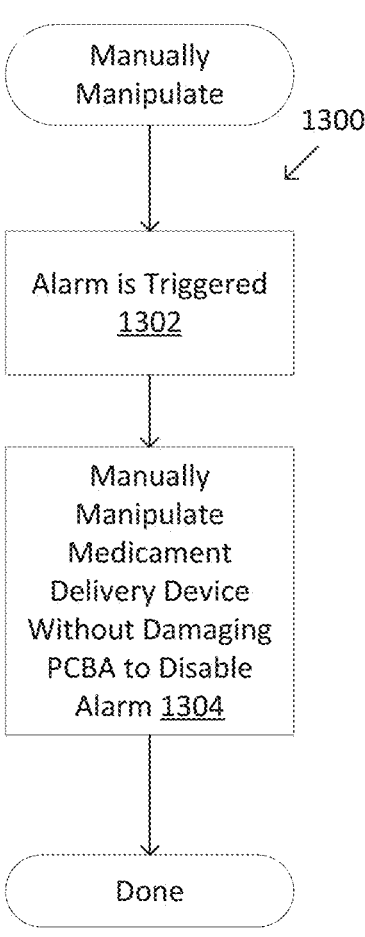
FIG. 13 depicts a flowchart of illustrative steps that may be performed in exemplary embodiments to shut off the alarm by manual manipulation of the medicament delivery device.

The alarm 216 also be shut off in some exemplary embodiments by manually manipulating the medicament delivery device 200. FIG. 13 depicts a flowchart 1300 of illustrative steps that may be performed in exemplary embodiments to disable the alarm 216 in this fashion. At 1300, the alarm 216 is triggered. At 1304, the medicament delivery device 200 is manually manipulated to shut off the alarm 216. The manual manipulation is such that the manipulation does not damage the PCBA.

Figure 14:
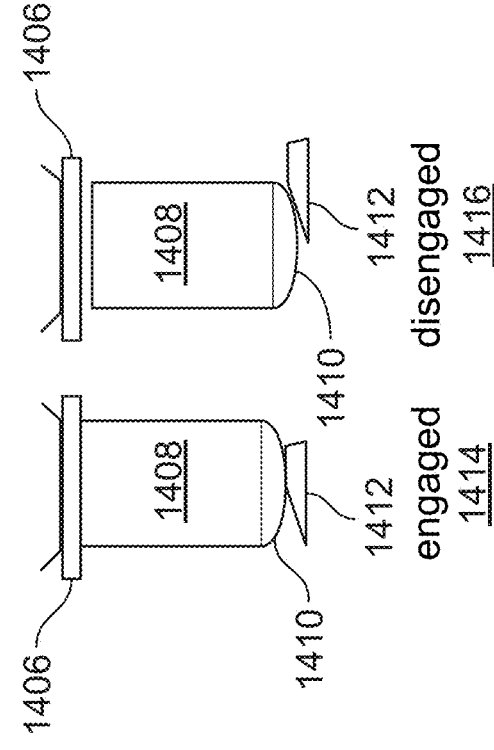
FIG. 14 depict a seventh exemplary embodiment that shuts off the alarm by manual manipulation of a knob to mechanically isolate an alarm.
Figure 14:
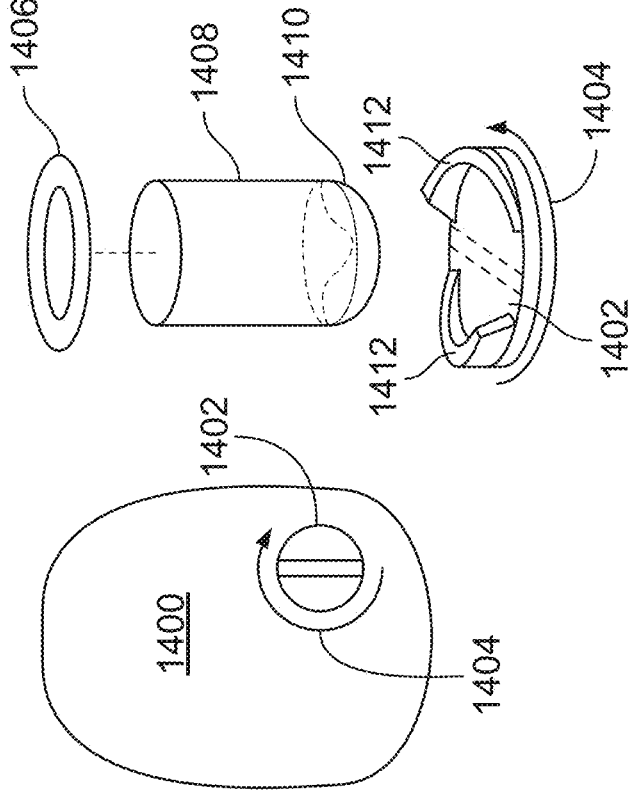

FIG. 14 depicts a seventh exemplary embodiment, which is an example of an arrangement where the medicament delivery device 1400 may be manually manipulated to disable the alarm 216. As shown, the bottom housing 1400 of the medicament delivery device includes a knob 1402, that may be turned by the user. The turning of the knob 1402 causes the inclined surfaces 1404 on the interior facing side of the knob 1402 to rotate in direction of arrow 1404. The rotation rotates the inclined surfaces 1412 relative to the bottom portion 1410 of a compressed beam 1408. During normal operation of the medicament delivery device 200, the piezoelectric element 1406 that serves as the alarm 216 is in the engaged state 1414 as shown, where the piezoelectric component 1406 is mechanically engaged with the compressed beam 1408. In the engaged state 1414, the lower portion 1410 of the compressed beam 1408 contacts the most raised portion of the inclined surfaces 1412. However, when the knob is rotated clockwise in the direction of arrow 1404, the bottom surface 1410 of the compressed beam 1408 contacts the least inclined portions of the inclined surfaces 1412 and enters the disengaged state 1416. Conversely, rotating the knob counterclockwise may cause the piezo-electric element to enter the engaged state 1414. Thus, this embodiment shuts off the alarm 216 by mechanically isolating or decoupling the alarm 216 so that activating the alarm does not result in an alarm output.

Figure 15A:
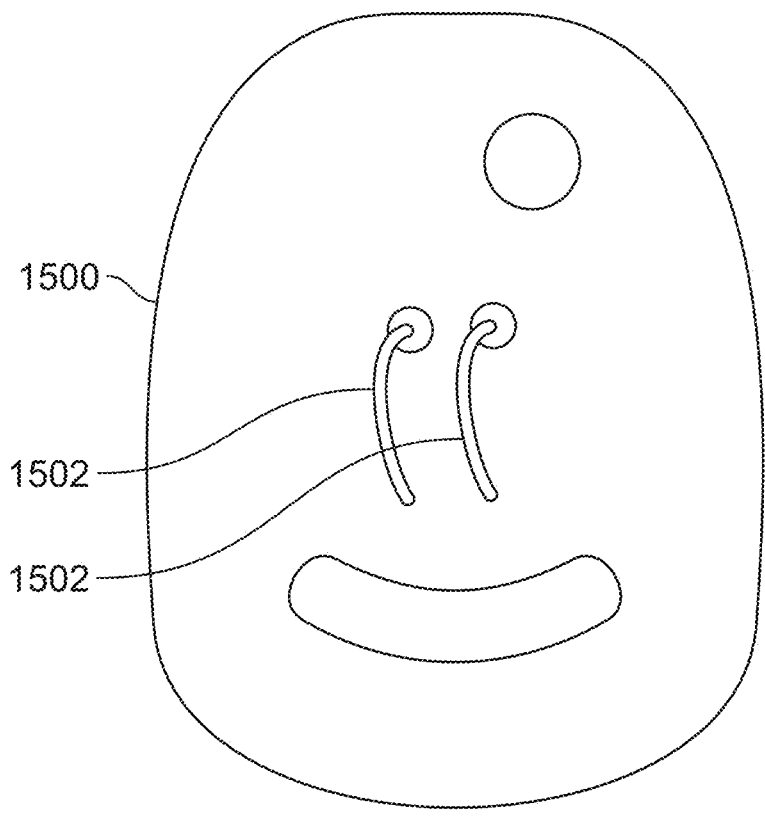
FIG. 15A depicts an eight exemplary embodiment that uses capacitance sensing electrodes.
Figure 15B:
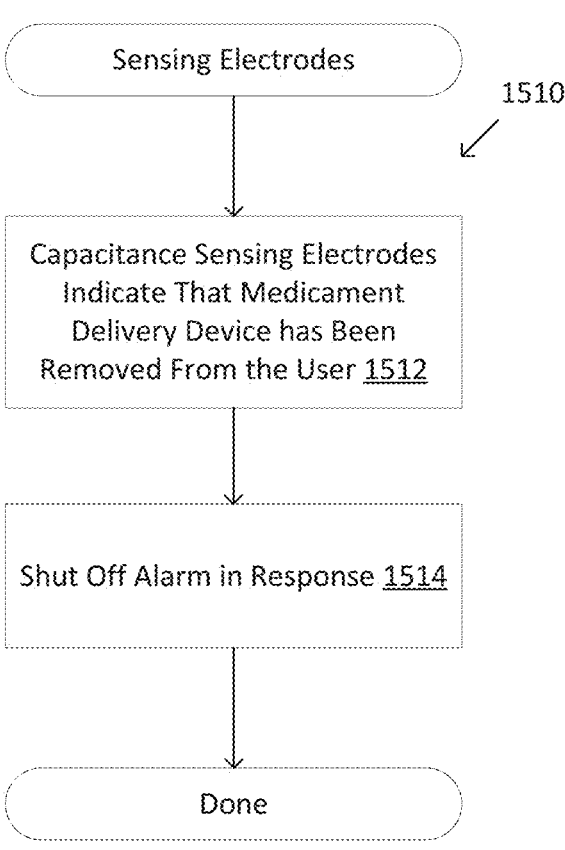
FIG. 15B depicts a flowchart of illustrative steps that may be performed in exemplary embodiments to shut off the alarm responsive to the capacitance sensing electrodes sensing that the medicament delivery device has been removed from the skin of the user.

FIG. 15A depicts an eighth exemplary embodiment. In this exemplary embodiment, capacitance sensing electrodes 1502 are molded into the bottom housing 1500 of the medicament delivery device 200. These capacitance sensing electrodes 1502 sense capacitance. The capacitance changes when the medicament delivery device is removed from the skin of the user. This change may be detected and used in shutting off the alarm 216. As shown in the flowchart 1510 of FIG. 15B, at 1512, the capacitance detected by the capacitance sensing electrodes 1502 indicate that the medicament delivery device 200 has been removed from the skin of the user. At 1514, the alarm 216 is shut off in response.

While exemplary embodiments have been described herein, various changes in form and detail may be made without departing from the intended scope of the attached claims.

The invention claimed is:

1. A medicament delivery device, comprising:
a printed circuit board containing electronic components;
an alarm for creating an alarm sound and/or vibration;
an electrical circuit for carrying electricity to the alarm, wherein at least a portion of the electrical circuit is on the printed circuit board;
an electrically conductive element that is electrically connected to the electrical circuit, is separate from the printed circuit board, and is displaceable in response to a force to be no longer electrically connected to the electrical circuit without harming the printed circuit board;
a housing for housing the printed circuit board, alarm element, and electrically conductive element; and
a passage through the housing leading to the electrically conductive element, the passage is adapted for receiving a tool to apply the force to displace that electrically conductive element so that the electrically conductive element is no longer connected to the electrical circuit.

2. The medicament delivery device of claim 1, wherein the electrically conductive element is coupled to a plug that fits in a portion of the passage that is displaced by the force of the tool, which in turn displaces the electrically conductive element so as to be no longer electrically connected to electrical circuit.

3. The medicament delivery device of claim 2, wherein the plug has deformable components that deform responsive to the force from the tool.

4. The medicament delivery device of claim 1, wherein the printed circuit board includes an at least partially plated through hole that is part of the passage and the electrically conductive element is positioned in the at least partially plated through hole to be electrically connected to the electrical circuit.

5. The medicament delivery device of claim 4, wherein the electrically conductive element is configured to be displaced out of the at least partially plated through hole by the force of the tool so as to no longer be electrically connected to the electrical circuit.

6. The medicament delivery device of claim 5, wherein the electrically conductive element is a sheet metal clip having a first portion positioned in the at least partially plated through hole and a second portion connected to another element in the electrical circuit.

7. The medicament delivery device of claim 5, wherein the electrically conductive element is a clip that fits at least partially inside the at least partially plated through hole and is biased to contact plated walls of the plated through hole.

8. The medicament delivery device of claim 1, wherein the electrically conductive element is a pin held between electrically conductive surfaces that is displaced to no longer be held between the electrically conductive surfaces by the force.

9. The medicament delivery device of claim 8, wherein the electrically conductive surfaces are parts of the sheet metal clips.

10. The medicament delivery device of claim 1, wherein the medicament delivery device includes a chassis for the printed circuit board, wherein the electrically conductive element is a sheet metal clip connected at one end to the housing and at another end to at least one electrically conductive component on the printed circuit board, and wherein the chassis presses the clip down onto the electrically conductive component.

11. The medicament delivery device of claim 10, wherein the sheet metal clip is adapted to become dislodged from the chassis and to no longer be electrically connected to the electrical circuit when displaced by the force.

12. The medicament delivery device of claim 1, wherein there is a plated through hole in the printed circuit board, wherein the electrically conductive element is a sheet metal clip having a formed feature that plugs into the plated through hole to close the electrical circuit, and wherein the force displaces the formed feature from the plated through hole so that the electrically conductive element is no longer electrically connected to the electrical circuit.

13. A medicament delivery device, comprising:
a printed circuit board containing electronic components;
an alarm for creating an alarm sound and/or vibration;
an electrical circuit for carrying electricity to the alarm, wherein at least a portion of the electrical circuit is on the printed circuit board;
an electrically conductive element that is
electrically connected to the electrical circuit,
separate from the printed circuit board, and
breakable in response to a force to break an electrical connection to the electrical circuit without harming the printed circuit board;
a housing for housing the printed circuit board, alarm, and electrically conductive element; and
a passage through the housing leading to the electrically conductive element, the passage is adapted for receiving a tool to apply the force to break the electrically conductive element so that the electrically conductive element is no longer connected to the electrical circuit.

14. The medicament delivery device of claim 13, wherein the electrically conductive element is a sheet metal connector.

15. The medicament delivery device of claim 14, wherein the sheet metal connector has at least one tapered end for breaking when the force of the tool is applied.

16. The medicament delivery device of claim 15, wherein the sheet metal connector is configured to have breakpoints for breaking when the force of the tool is applied.

* * * * *